United States Patent
Paolinelli

(10) Patent No.: US 11,630,096 B2
(45) Date of Patent: Apr. 18, 2023

(54) PHASE WETTING DETECTION AND WATER LAYER THICKNESS CHARACTERIZATION IN MULTIPHASE OIL-WATER AND OIL-WATER-GAS FLOW

(71) Applicant: Ohio University, Athens, OH (US)

(72) Inventor: Luciano Daniel Paolinelli, Athens, OH (US)

(73) Assignee: Ohio University, Athens, OH (US)

( * ) Notice: Subject to any disclaimer, the term of this patent is extended or adjusted under 35 U.S.C. 154(b) by 380 days.

(21) Appl. No.: 16/488,619

(22) PCT Filed: Mar. 7, 2018

(86) PCT No.: PCT/US2018/021312
§ 371 (c)(1),
(2) Date: Aug. 26, 2019

(87) PCT Pub. No.: WO2018/165274
PCT Pub. Date: Sep. 13, 2018

(65) Prior Publication Data
US 2020/0041397 A1  Feb. 6, 2020

Related U.S. Application Data

(60) Provisional application No. 62/467,918, filed on Mar. 7, 2017.

(51) Int. Cl.
*G01N 33/28* (2006.01)
*G01N 27/02* (2006.01)
*G01F 23/24* (2006.01)

(52) U.S. Cl.
CPC ......... *G01N 33/2847* (2013.01); *G01N 27/02* (2013.01); *G01F 23/242* (2013.01)

(58) Field of Classification Search
CPC ...... G01F 23/22; G01F 23/242; G01F 23/244; G01N 27/02; G01N 27/04; G01N 27/06; G01N 27/07; G01N 27/08; G01N 33/2847
See application file for complete search history.

(56) References Cited

U.S. PATENT DOCUMENTS 8,054,091 B2 * 11/2011 Bhattacharjee .... G01N 33/2847
324/698
8,054,094 B1 * 11/2011 Langoju ................. G01N 27/02
324/705

(Continued)

FOREIGN PATENT DOCUMENTS

JP    2009216618 A  *  9/2009

OTHER PUBLICATIONS

ISA/US, International Search Report and Written Opinion issued in corresponding PCT Application No. PCT/US18/21312, dated May 14, 2018 (10 pages).

(Continued)

*Primary Examiner* — Justin N Olamit
(74) *Attorney, Agent, or Firm* — Wood Herron & Evans LLP

(57) ABSTRACT pa In one embodiment, a method of monitoring fluid flow includes mounting at least one probe including at least two electrodes to a conduit having a mixture including at least oil and water flowing therethrough and exciting the at least two electrodes with an AC voltage and a predetermined frequency. The method also includes measuring an impedance between the at least two electrodes and detecting a water layer based on the measured impedance. The mixture may also include gas. In another embodiment, a method of detecting phase wetting in a pipe includes measuring a high (Continued)

frequency impedance response of a two concentric electrode probe flush mounted in the pipe.

13 Claims, 21 Drawing Sheets

(56) References Cited

U.S. PATENT DOCUMENTS

| | | | | |
|---|---|---|---|---|
| 9,173,600 | B2* | 11/2015 | Matsiev | A61B 5/4839 |
| 10,197,546 | B2* | 2/2019 | Rahaliou | G01N 33/2847 |
| 2013/0265063 | A1* | 10/2013 | Cherney | G01N 27/06 |
| | | | | 324/695 |
| 2019/0162067 | A1* | 5/2019 | Benimeli | G01V 3/20 |

OTHER PUBLICATIONS

Rashedi, A, A study of surface wetting in oil-water flow in inclined pipeline. Doctoral dissertation, Ohio University. Apr. 2016. [Retrieved from the internet on Apr. 18, 2018]. <URL: https://etd.ohiolink.edeetd.send_file?accession=ohiou1448364959&disposition=inline>; abstract; pp. 29, 52, 65-67, 71-73, 77, 87, 136.

Lou, X et al., Controlling the morphology and uniformity of a catalyst-infiltrated cathode for solid oxide fuel cells by tuning wetting property. Journal of Power Sources, vol. 195, pp. 419-424. Aug. 5, 2009; abstract; p. 420.

Obrutsky, LS et al., Transmit-receive eddy current probes. IAEA, editor. Corende, vol. 3, pp. 167-175. 1997; abstract; pp. 170, 174.

Taitel, Yet al., Stratified three phase flow in pipes. International Journal of Multiphase Flow, vol. 21, No. 1, pp. 53-60. Dec. 1, 1995; abstract; pp. 53-54, 56.

Qiu, Yet al. Real-time monitoring primary cardiomyocyte adhesion based on electrochemical impedance spectroscopy and electrical cell-substrate impedance sensing. Analytical Chemistry, vol. 80, No. 4, pp. 990-996. Feb. 15, 2008; abstract; p. 991.

Marchebois, H et al. Zinc-rich powder coatings characterisation in artificial sea water EIS analysis of the galvanic action. Electrochimica Acta, vol. 49, pp. 1719-1729. 2004; p. 1720.

* cited by examiner

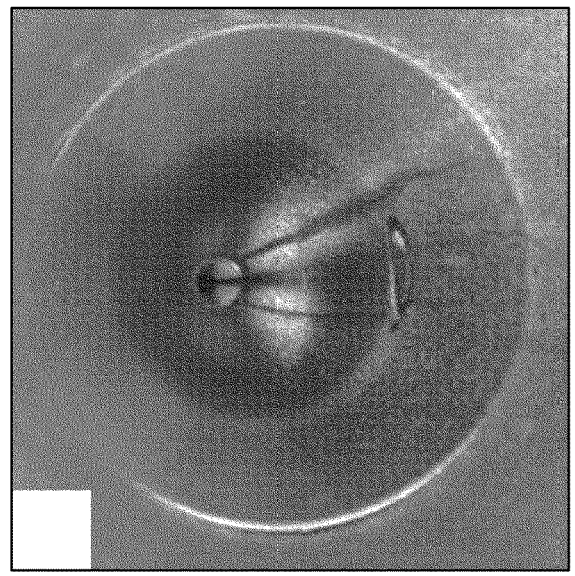
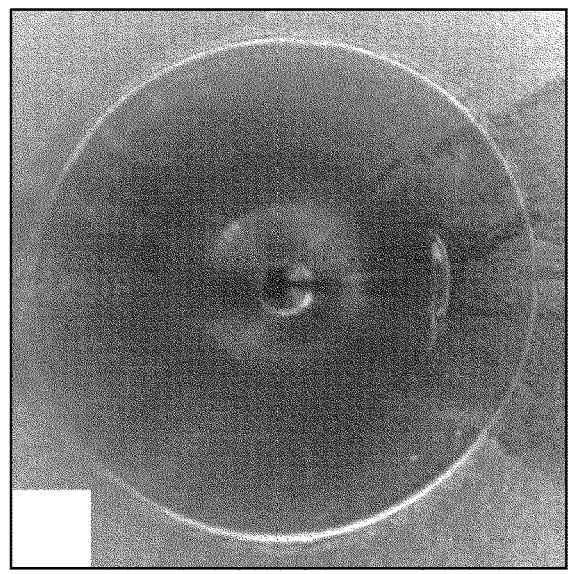
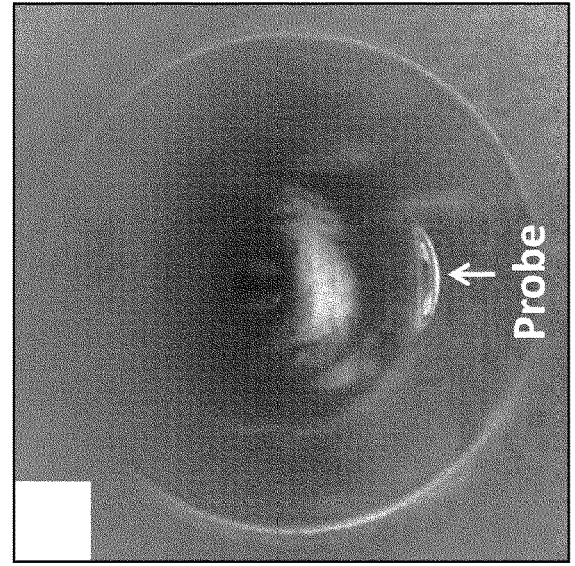
FIG. 9C
FIG. 9B
FIG. 9A

PHASE WETTING DETECTION AND WATER LAYER THICKNESS CHARACTERIZATION IN MULTIPHASE OIL-WATER AND OIL-WATER-GAS FLOW

CROSS-REFERENCE TO RELATED APPLICATIONS

This application claims priority to co-pending International PCT Application No. PCT/US2018/021312 filed on Mar. 7, 2018, which claims the benefit of U.S. Provisional Application Ser. No. 62/467,918 filed on Mar. 7, 2017, the disclosures of which are expressly incorporated by reference herein in their entireties.

TECHNICAL FIELD

The invention relates to phase wetting in multi-phase oil-water and oil-water-gas flow and, more particularly, to a method for detecting phase wetting in multi-phase oil-water and oil-water-gas flow and for determining the water layer thickness associated with water wetting.

BACKGROUND

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Multiphase flow of liquid hydrocarbons and water (e.g., two-phase flow of liquid hydrocarbons and water, and three-phase flow of liquid hydrocarbons, water, and gas) is commonly found in several industrial processes, such as in pipelines, risers, tubes, vessels, and tanks associated with oil production facilities. In such cases, contact between water and internal pipe wall can be a great concern, since it can lead to serious corrosion problems, particularly when materials such as carbon steel are used. This scenario is called water wetting. It is considered that under regular production conditions the hydrocarbon phase is not corrosive. Therefore, if the water phase is disrupted and entrained into the turbulent oil phase flow, water wetting and internal corrosion risks can be avoided. Determining phase wetting regimes in multi-phase hydrocarbon-water pipe flow can thus be instrumental in corrosion engineering, such as by providing information regarding which operating conditions can minimize or increase the risk of internal corrosion.

In addition, the thickness of water layers in contact with the pipe wall is an important parameter that can be used to estimate the internal corrosion rate of the pipe. For example, mass transfer of corrosive species to the pipe surface is affected by the velocity of the water layer, which is proportional to its thickness. Moreover, very thin water layers can flow so slowly and be so poorly replenished by the dispersed water droplets that they get rapidly saturated with dissolved metallic ions (e.g., ferrous ions) from the occurring corrosion processes. Under this circumstance, corrosion products can then precipitate forming a protective barrier which reduces corrosion rate.

It would therefore be desirable to provide a method for detecting phase wetting in multi-phase oil-water and oil-water-gas flow and for determining the water layer thickness associated with water wetting to enable personnel such as corrosion and integrity engineers to take timely corrective/preventative measures, such as the addition of corrosion inhibitors or change of flow rates or fluid velocities, to maintain the reliability of their facilities and reduce maintenance costs.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

In one embodiment, a method of monitoring fluid flow includes mounting at least one probe including at least two electrodes to a conduit having a mixture including at least oil and water flowing therethrough and exciting the at least two electrodes with an AC voltage and a predetermined frequency. The method also includes measuring an impedance between the at least two electrodes and detecting a water layer based on the measured impedance.

In another embodiment, a method of detecting phase wetting in a pipe includes measuring a high frequency impedance response of a two concentric electrode probe flush mounted in the pipe.

BRIEF DESCRIPTION OF THE DRAWINGS

Various additional features and advantages of the invention will become more apparent to those of ordinary skill in the art upon review of the following detailed description of one or more illustrative embodiments taken in conjunction with the accompanying drawings. The accompanying drawings, which are incorporated in and constitute a part of this specification, illustrate one or more embodiments of the invention and, together with the general description given above and the detailed description given below, serve to explain the one or more embodiments of the invention.

FIGS. 9A-9C are photographs of the internal surface of the carbon steel test section of the flow loop of FIG. 4, wherein FIG. 9A depicts the polished fresh surface, FIG. 9B depicts the surface after 30 minutes of horizontal oil-water flow with 1.7 m/s mixture velocity and 3% water cut, and FIG. 9C depicts the surface after 30 minutes of horizontal oil-water flow with 3.7 m/s mixture velocity and 3% water cut.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
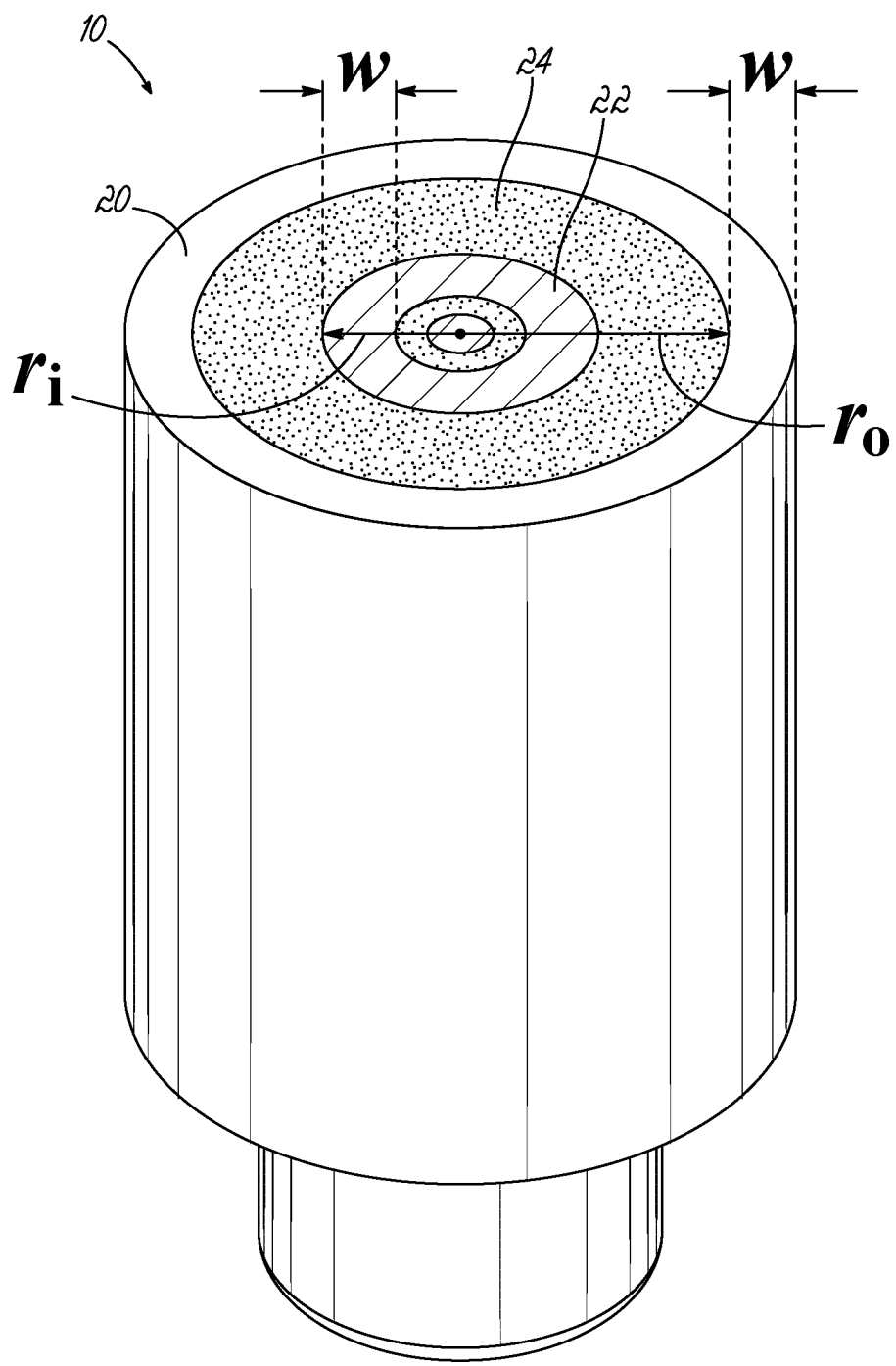
FIG. 1 is a perspective view of an exemplary two electrode high frequency impedance probe in accordance with an aspect of the present invention.

Referring now to FIG. 1, an exemplary impedance probe 10 may be installed in a section 12 of a conduit, such as a pipe 14 (FIGS. 4 and 5), through which a mixture including at least oil and water flows in accordance with an aspect of the invention. As discussed in greater detail below, the probe 10 may be constructed as a two concentric electrode probe capable of resisting high pressure, temperature, and corrosion generated by produced fluids in the oil and gas industry. For example, the probe 10 may use low voltage, such as less than 50 mV rms, and high frequency, such as greater than or equal to 20 kHz, AC excitation. In accordance with an aspect of the invention, the current flowing through the probe 10 is measured and its impedance is calculated and analyzed to determine whether water phase is wetting the wall of the section 12 and/or to determine the thickness of the water layer. Such measurements may be performed in less than a fraction of a second, such as less than 0.5 second, and the results may be transmitted online via wire or radio frequency to a monitoring station where the information can be analyzed in real time. In this manner, the present invention may provide early detection of segregated water in contact with internal pipe surfaces, as well as a measurement of the segregated volume of water via the detected water layer thickness. The method may be non-intrusive for multiphase pipe flow and, therefore, may avoid producing erroneous results such as artificial water segregation or entrainment. Once mounted, the probe 10 may require little or no maintenance. In addition, the probe 10 may be suitable for off-shore operation. The provided online water wetting and water layer thickness data may enable personnel such as corrosion and integrity management engineers to take timely and informed measures against corrosion and other water related damage risk for pipelines or other facilities. Unlike corrosion sensors such as electrical resistance sensors and simple coupons, which take significant time to provide relevant data and do not provide any online information regarding the existence of water in contact with the actual pipe surface or the segregated water volume, the probe 10 is capable of providing both water wetting and water layer thickness data nearly instantaneously. Moreover, the probe 10 may be used in a variety of facilities such as flowlines, pipelines, risers, manifolds, storage vessels, and tanks, and in a variety of industries such as oil and gas, petrochemical, pharmaceutical, food products, and other industries involving water as a corrosive fluid. The features of the probe 10 and related methods of detecting phase wetting and water layer thickness are set forth in further detail below to clarify each of these functional advantages and other benefits provided in this disclosure.

The illustrated probe 10 is configured for installation in large scale industrial conduits such as the section 12 of pipe 14, more particularly, to be positioned flush-mounted with the internal wall of the section 12. The probe 10 comprises two-electrode concentric contacts, including an outer ring 20 and an inner ring 22, which are separated by an insulator 24. The rings 20, 22 may each be constructed of a corrosion resistant alloy, such as stainless steel. In one embodiment, the outer ring 20 may be constructed of stainless steel and the inner ring 22 may be constructed of carbon steel. The insulator 24 may be constructed of epoxy, such as a polymer resin, or a ceramic material. In one embodiment, the internal radius $r_o$ of the outer ring 20 may be approximately 12.5 mm and the external radius ri of the inner ring 22 may be approximately 6.2 mm. The two electrodes 20, 22 may have the same width w, which may be, for example, approximately 3 mm.

In oil-water flow water wetting studies, it is of interest to detect when water is no longer stably dispersed in oil and drops out due to the effect of gravity leading to rivulets or water layers forming at the bottom wall of the section 12 of the pipe 14. In this scenario, the impedance probe 10 can sense the constant or alternating presence of a water film or layer covering completely or partially its contacts 20, 22. In this regard, the total measured impedance Zt can be defined as the impedance Zp of the probe 10 considered in parallel with the impedances of the fluids on top of the contacts 20, 22, namely, the impedance $Z_w$ of a water layer, the impedance $Z_o$ of an oil layer, and/or the impedance $Z_m$ of a water-in-oil mixture layer. The oil or the water-in-oil mixture layer may present very low capacitance and very high resistance compared to the probe 10 itself or the water layer. Therefore, when the probe 10 is wetted by an oil or water-in-oil mixture layer, the total measured impedance is Zt=Zp since the impedance of the liquid is sufficiently high so that it does not affect the measurement. When a water layer is present, the total measured impedance can be expressed as:

$$Z_t = [Z_p^{-1} + Z_w^{-1}]^{-1} \qquad (1)$$

Fundamentally, the probe 10 responds as a capacitor at high and middle frequency range, thus:

$$Z_p = -(2\pi f C_p)^{-1} j \qquad (2)$$

where f is the frequency of the AC excitation and Cp is the total capacitance of the probe 10.

Figure 2:
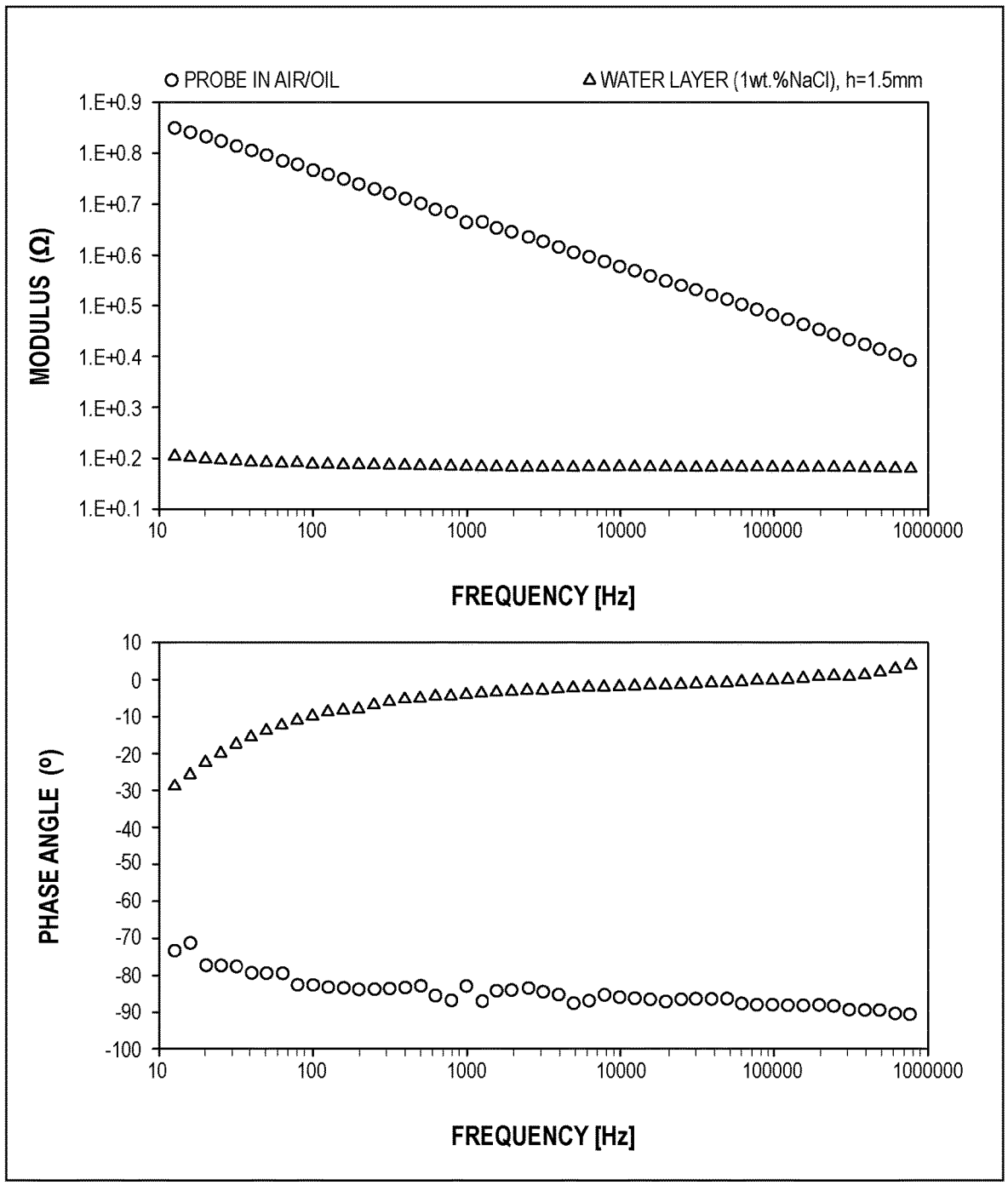
FIG. 2 is a Bode plot of the impedance frequency response of the probe of FIG. 1 in air or oil and with a conductive water layer on top of the probe.

In general, the impedance of a conductive water layer consists only of a real part at high frequencies (resistive behavior). Moreover, its value is usually substantially low relative to the probe 10. In this case, equation (1) shows that the total measured impedance is only due to the presence of water ($Z_t \cong Z_w = R_s$). FIG. 2 shows the Bode plot of the typical frequency response of the probe 10 alone and with a conductive water layer on top. At mid/low frequencies, the effect of the electrochemical double layer at the electrode surfaces 20, 22 becomes important when water is present, adding capacitive impedance. It is clear that to avoid the effect of Faradaic impedance in this system, frequencies higher than 1 kHz may be used.

The resistive response of a very thin water layer of thickness h that covers the probe 10 surface uniformly can be estimated as:

$$R_s = \frac{1}{\kappa} \frac{\ln(r_o/r_i)}{2\pi h} \qquad (3)$$

where κ is the conductivity of the liquid.

At this point, a simple quantitative verification of the assumptions made on the contributions of the impedances of a water layer, oil layer, and the probe 10 on the total measured impedance can be performed. For example, if a 1 mm thickness liquid layer is placed on top of the probe 10, its characteristic geometric constant ($K=\ln(r_o/r_i)/2\pi h$) may be approximately 110 $m^{-1}$. If the layer is considered as tap water (electric conductivity $\kappa \sim 0.05$ S $m^{-1}$, and dielectric permittivity $\varepsilon \sim 700 \times 10^{-12}$ F $m^{-1}$), its resistance (R=K/κ) may be approximately 2200Ω and its capacitance (C=ε/K) may be approximately $6.3 \times 10^{-12}$ F. On the other hand, if the layer is considered as oil (electric conductivity $\kappa \sim 10 \times 10^{-12}$ S $m^{-1}$ and dielectric permittivity $\varepsilon \sim 20 \times 10^{-12}$ F $m^{-1}$), its resistance may be approximately $5.5 \times 10^{12}$ and its capacitance may be approximately $1.8 \times 10^{-13}$ F. Comparison of the resistance and capacitance values of the above considered layers with the electrical properties of the probe 10 (having, in the exemplary embodiment, capacitance of approximately $2 \times 10^{-11}$ F without wiring and resistance $>1 \times 10^9 \Omega$ as illustrated in FIG. 2), both the resistance of the water layer and the capacitance of the probe 10 may be the dominant contributing factors to the total measured impedance at high frequency. If a water-in-oil mixed layer is considered, its electrical properties do not vary significantly with the dispersed water volume fraction respect to the oil alone. Therefore, the conclusions relating to the quantitative analysis above hold true.

To quantify the resistance of the larger water layer thicknesses, a theoretical solution for flush mounted parallel rectangular electrodes can be adapted for the illustrated concentric electrode probe 10; where the mean length of the electrodes array is $l=\pi(r_o+r_i)$; and the insulator half-width is $\alpha=(r_o-r_i)/2$. Therefore, the dimensionless thickness of the water layer is expressed as:

$$h^* = h/\alpha = 2h/(r_o-r_i); \qquad (4)$$

and the dimensionless half-distance between the end edge of each electrode 20, 22 is:

$$\lambda_i = \lambda_o = \lambda = w/\alpha + 1 = 2w/(r_o-r_i) + 1 \qquad (5)$$

Figure 3:
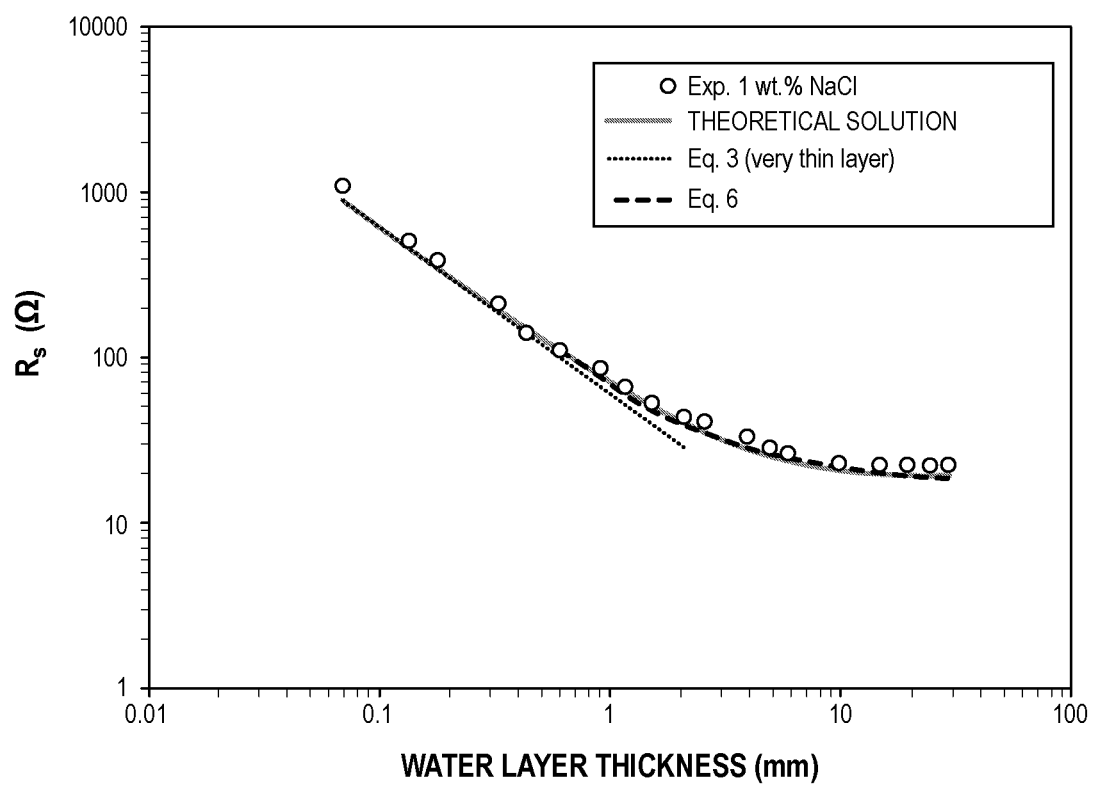
FIG. 3 is a plot of the measured resistance of various water layers ($R_S$) as a function of their thickness showing comparisons with analytical expressions.

FIG. 3 shows the theoretical resistance estimated using this solution adapted to the concentric electrode geometry (solid line) and "experimental values" for different water layer thicknesses (circles) in a static state. For the experimental values, exact water layer thicknesses were obtained using a parallel flat PVC piece separated by calibrated spacers on top of the probe 10. Water layer resistance was measured by exciting the probe 10 with an AC voltage of 10 mV rms and frequency of 20 kHz using a Gamry REF 600® potentiostat. The aqueous electrolyte was a 1 wt % NaCl solution prepared from an analytical grade reagent and deionized water, with a measured conductivity (κ) of 1.76 S $m^{-1}$ at 25° C.

The flush-mounted probe 10 may have a depth sensing upper threshold of ca. 10 mm, as illustrated in FIG. 3. The adapted analytical solution agrees very well with experimental data (average difference of 10%); therefore, the probe 10 does not require empirical calibration to relate h with the measured resistance $R_S$. However, since the analytical solution arises from the quotient of the solutions of two complete elliptic integrals, it presents a very complicated form when expressed as a function of the thickness of the conductive layer. Here, a simple convenient approximation of the exact solution is given as a function of the water layer thickness and the inner and outer radius of the concentric electrodes 20, 22 for $\lambda_i = \lambda_o = \lambda = 2$.

$$R_s = \frac{1}{\kappa \pi (r_o + r_i)} \left[ 1.89 + \frac{1.46}{\left( \frac{2h}{(r_o - r_i)} - 0.5 \right)} \right] \qquad (6)$$

Equation (6) reproduces the analytical solution with no more than 5% error for dimensionless thicknesses (h*) equal to or larger than 0.2 (dashed line in FIG. 3). Equation (3) can be used for h* values lower than 0.2 with error below 5% (dotted line in FIG. 3).

The measured resistance values are determined with a maximum uncertainty lower than 5%, and water conductivity is considered to vary no more than 5% mainly due to fluctuations in temperature (for example, from 25° C. to 22° C.). Differentiating equation (6) with respect to the layer thickness h, it can be estimated that, for the exemplary probe dimensions, accurate determination of the thickness of a conductive layer is limited to approximately 5 mm, where the maximum total error reaches around 20%.

In one embodiment, the surface of the probe 10 configured to face the interior of the pipe 14 may be machined to fit the curvature of the pipe 14 so that the probe 10 may be flush-mounted to the section 12 of pipe 14. A mixture including at least oil and water may flow through the pipe 14, and phase wetting and water layer thickness measurements may be performed in dynamic conditions in the oil-water flow. Electrical measurements with the probe 10 may be with an AC voltage between approximately 5 mV rms and approximately 500 mV rms and a frequency between approximately 10 kHz and approximately 1 MHz. The frequency may be high enough to avoid the interference of Faradaic impedance at the surfaces of the electrodes 20, 22 on the measurements. The probe 10 may be coupled to a potentiostat, such as a Gamry REF 600® potentiostat (not shown), which may have a computer interface. Impedance measurements may be performed substantially continuously with a relatively short sampling rate, such as approximately 0.5 second.

The oil and water phases may be any desired oil and water phases. In one embodiment, the oil phase may be a clear saturated paraffinic hydrocarbon such as Isopar V® and the water phase may be a 1 wt % NaCl solution.

For relatively large flow mixture velocities, the impedance measurements by the probe 10 may show capacitive behavior similar to when oil-only flow is measured. This may indicate that all the transported water is entrained and the interior surface of the wall of the section 12 of pipe 14 is only in contact with oil. For lower mixture velocities, the measured impedance modulus may decrease and the phase angle may increase, which may indicate the presence of water wetting the wall of the section 12 of pipe 14. Lower impedance modulus and a phase angle approaching zero degrees (resistive behavior) may be an indication that thicker water layers may be present at the lower mixture velocities.

Estimations of the thickness of the water layers may be performed using equations (1)-(3) and (6). The calculated values may correspond to the average thickness of the water layer flowing on top of the concentric area between the electrodes 20, 22 of the probe 10. The measured impedance signal may be processed substantially instantaneously after it is obtained, which may allow characterization of water layer thicknesses not only in situ but also in terms of how they evolve in real time. The smallest detectable water layer thickness may depend on the intrinsic impedance of the probe 10, the conductivity of the water, and the noise level of the measured electrical signal (which may be inherent to the quality of the electronic measurement device and/or wiring). The minimum detectable water layer thickness may be reduced regardless of the intrinsic electrical noise of the measurement by increasing either the water conductivity or the impedance of the probe 10 (low capacitance), which is a parameter that can be engineered jointly with the geometry of the electrodes 20, 22 to optimize the useful measurement range of the probe 10.

Figure 12A:
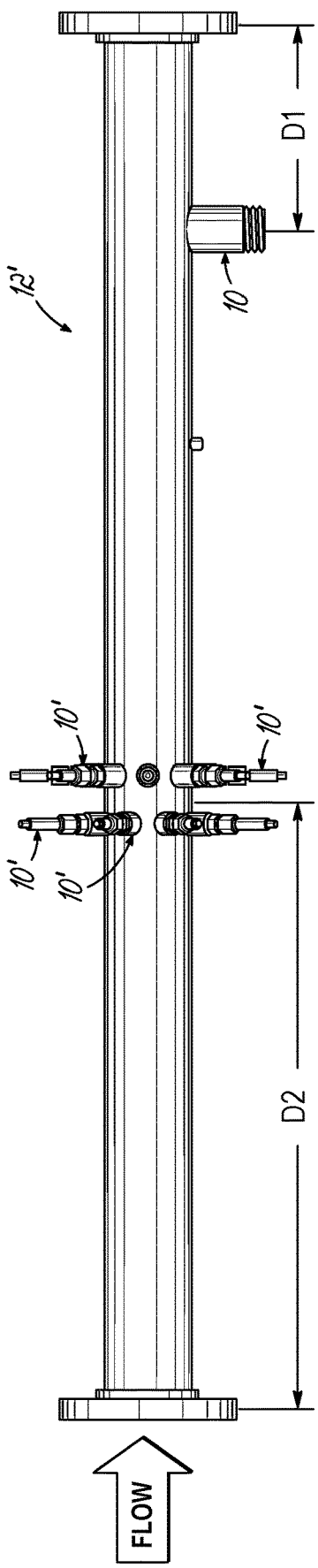
FIG. 12A is a side elevation view of the carbon steel test section of the flow loop of FIG. 11.
Figure 12B:
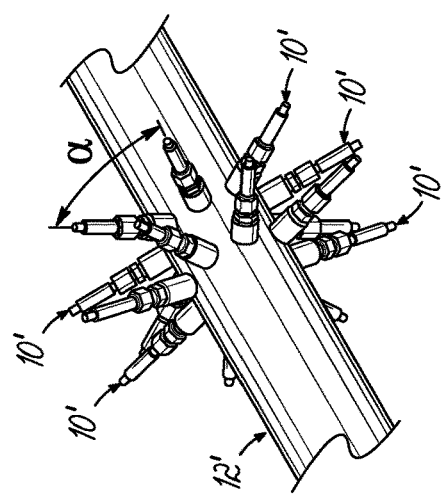
FIG. 12B is a partial perspective view of the carbon steel test section of the flow loop of FIG. 11.

In another embodiment, a plurality of probes 10, 10' of varying sizes may be used. For example, a relatively large probe 10 and an array of relatively small probes 10' may be machined to fit the curvature of a pipe 14 so that the probes 10, 10' may each be flush-mounted to the section 12 of pipe 14 (FIGS. 12A and 12B). A mixture including oil, water, and gas may flow through the pipe 14, and phase wetting and water layer thickness measurements may be performed in dynamic conditions in the oil-water-gas flow. Each of the probes 10, 10' may be operated separately with an AC voltage of between approximately 5 mV rms and approximately 500 mV rms and a frequency between approximately 10 kHz and approximately 1 MHz. The probes 10, 10' may be coupled to a potentiostat, such as a Gamry REF 600® potentiostat, which may have a computer interface. Impedance measurements may be performed substantially continuously with a relatively short sampling rate, such as approximately 0.5 second. The presence of water layers in contact with the probes 10, 10', and their thickness, may be determined from the measured impedance values (modulus and phase angle) in relation to the theoretical response of the probes 10, 10' and the electrical conductivity of the water phase, as discussed above.

The oil, water, and gas phases may be any desired oil, water, and gas phases. In one embodiment, the oil phase may be a clear saturated paraffinic hydrocarbon such as Isopar V® and the water phase may be a 1 wt % NaCl solution. The gas phase may be air.

The exemplary probe 10 and related methods may be used in various industrial applications. For example, they may be used in flowlines, pipelines, risers, and/or manifolds. In these applications, water separating from oil (and/or gas) can cause corrosion. Early indication of even thin layers may facilitate timely measures to address such corrosion. Moreover, emulsion formation or water drop out from emulsions can be detected. The occurrence of emulsions is typically only known at the inlet and outlet or, in some cases, only at the outlet of a conduit. By detecting water layers, the probe 10 can provide useful information at real time. The accumulation of water may also impede gas flow and form slugs. The detection of such accumulation also allows flow control and water sweep out measures.

The exemplary probe 10 and related methods may also be used in separators and/or knock-out vessels, such as in liquid collection (hydrocarbons/water) applications. Water collecting as a free phase can cause corrosion, which might be unexpected in low water cut systems, forming thin layers. Level detection allows control of bottom water level to avoid overflow.

The exemplary probe 10 and related methods may also be used in storage vessels and/or tanks intended for hydrocarbon storage. In such applications, water may accumulate over time at the bottom of the container and cause corrosion. Detection facilitates drainage measures when needed.

Free water phase and/or water layer thickness measurements can be integrated in integrity management, which is particularly powerful if combined with multi-phase models. This may allow proactive confirmation of model predictions in early stages, thereby reducing uncertainty and rendering management measures more robust and cost efficient. Measures could include corrosion inhibitor injection, drying, and/or flow regime change.

Example 1

In this example, the surface of the probe 10 configured to face the fluid flow is machined to fit the curvature of a 0.1 m ID pipe. The slight surface curvature can lead to over prediction of the conductive water layer. An analytical expression to estimate this difference for parallel electrodes with parallel curvature axes indicates a maximum deviation of 5% may be found for a conductive layer of 5 mm with a proportional decrease of the deviation for lower thicknesses. However, as the probe 10 has concentric design the actual deviation may be about a half of such an estimate.

Figure 4:
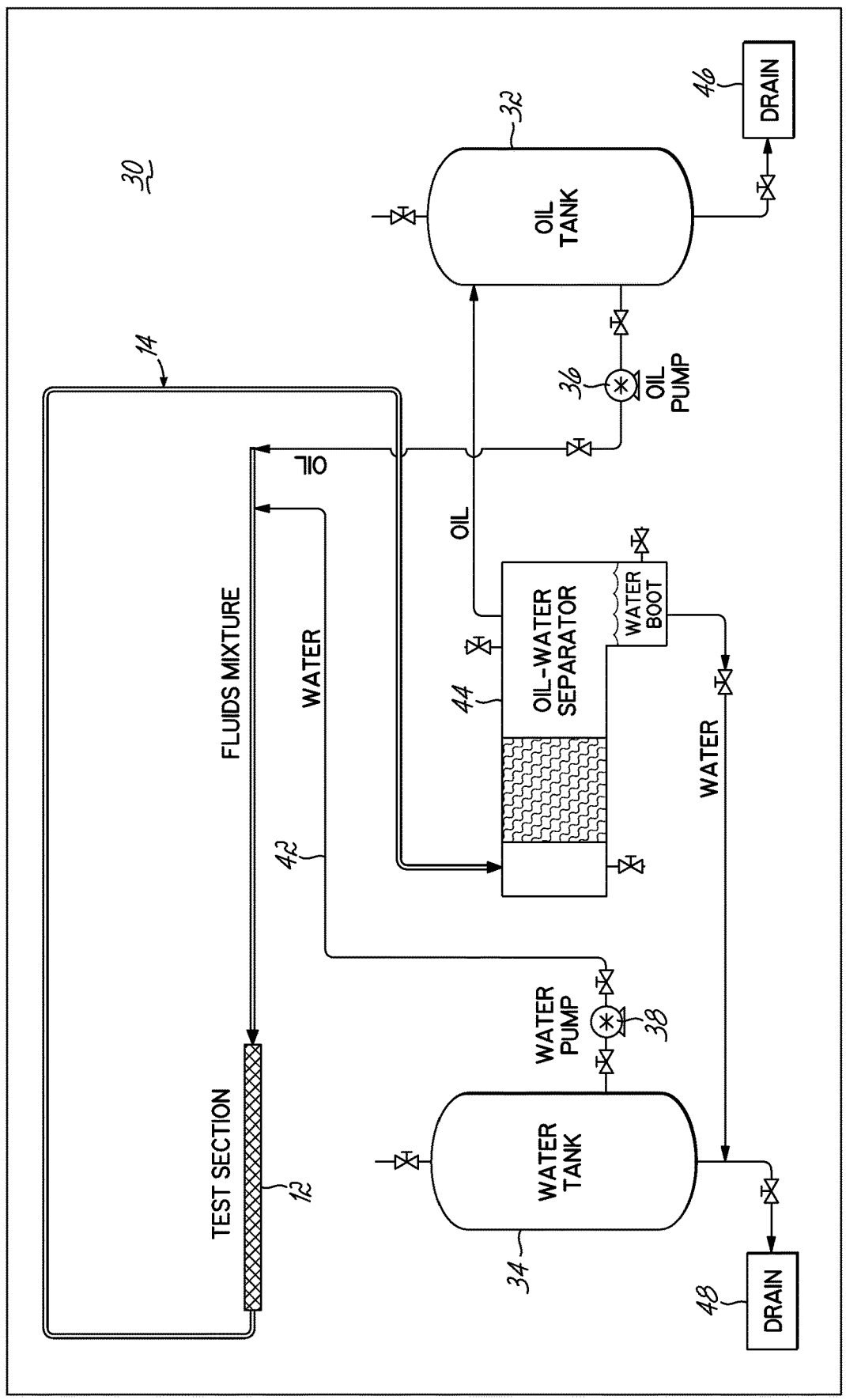
FIG. 4 is a schematic view of a flow loop used for oil-water flow tests in accordance with an aspect of the present invention.

Phase wetting and water layer thickness measurements were performed according to an aspect of the invention in dynamic conditions in oil-water flow using a large-scale fully inclinable multiphase flow loop 30. A schematic layout of the flow loop 30 is shown in FIG. 4. The main part of the loop 30 consists of a 30 m long, 0.1 m internal diameter (ID) flow line mounted on a steel rig structure (not shown). The loop consists of two parallel sections of pipe 14 connected by a 180-degree bend. Oil and water are injected separately from individual storage tanks 32, 34 (each one made of stainless steel and with a capacity of 1.2 m$^3$) into the 0.1 m ID main line 14 by progressive cavity pumps 36, 38. Flow rates of oil and water are monitored independently by flow meters (not shown) with an average accuracy of 10%. Water is injected into the main line 14 at a T-junction through a perpendicular 0.05 m ID secondary line 42. The fluid mixture first flows in a stainless steel pipe 14 (upstream leg) over a distance equivalent to approximately 140 pipe diameters allowing flow pattern and wall wetting to stabilize. The flow then enters a 1.8 m long carbon steel test section 12 where phase wetting measurements are carried out using the exemplary impedance probe 10 flush-mounted at a distance of 16 pipe diameters downstream from the inlet of the section 12. A clear acrylic section (not shown) is located immediately after the test section to allow visualization of the developed flow patterns. Upon exiting the main line 14, the mixture is directed to an oil-water separator 44 such that the separated oil and water streams may be returned to their respective storage tanks 32, 34 for further recirculation. Alternatively, the separated oil and water streams may be directed to respective drains 46, 48.

Before each experimental run, the internal surface of the test section 12 was polished using a rotating flexible abrasive tool (180 grit) with deionized water as the polishing fluid. The surface was then washed with deionized water and isopropanol, then dried with a clean cloth. The roughness of the polished surface of the test section 12 was indirectly measured using optical profilometry data, taken from the surface of an epoxy-mounted specimen with an area of about 5 cm$^2$ of the internal pipe wall. The measured average value in terms of arithmetic roughness (Ra) was 1.7 μm, with an average mean peak to valley distance (Rz) of about 10 μm.

Figure 5:
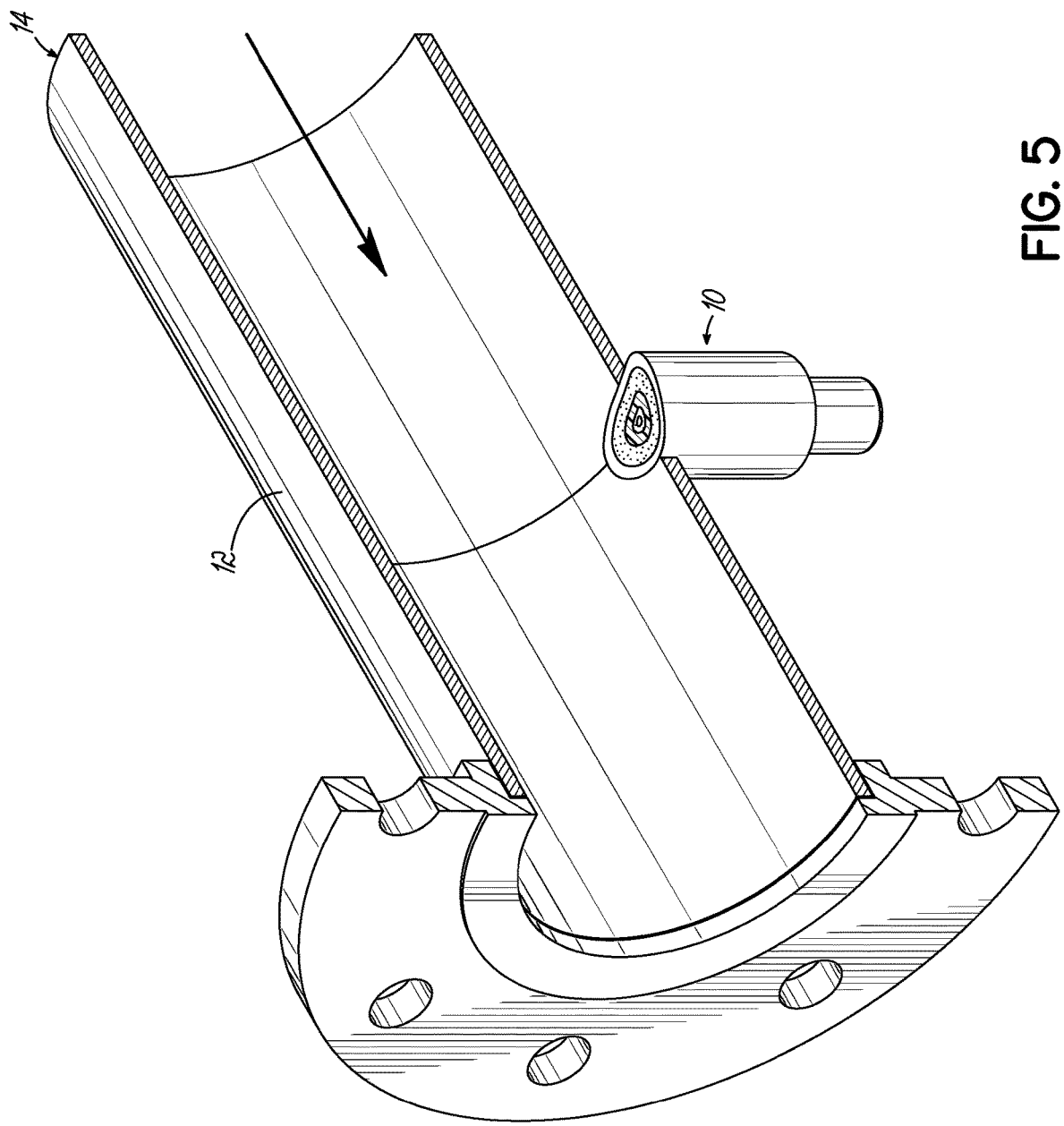
FIG. 5 is a partial cross sectional view of the test section of the flow loop of FIG. 4, wherein the direction of flow is indicated by the illustrated arrow.

Prior to introducing the impedance probe 10 in the test section 12, its exposed surface was polished with a 240 grit SiC paper and deionized water to assure the proper shape of the internal pipe curvature, and later alignment. The probe 10 was also rinsed with deionized water and isopropanol, then dried with a clean cloth. Subsequently, the impedance probe 10 was flush-mounted at the bottom of the carbon steel test section 12, as shown in FIG. 5, where water is most likely to segregate. The surface of the probe 10 never intruded the oil-water flow and its height misalignment with respect to the surface of the test section 12 was maintained lower than 0.1 mm.

Electrical measurements with the probe 10 were with an AC voltage of 10 mV rms and frequency of 20 kHz using a Gamry REF 600® potentiostat with a computer interface. The 20 kHz frequency is high enough to avoid the interference of Faradaic impedance at the surfaces of the electrodes 20, 22 on the measurements as can be inferred from FIG. 2. In the case thin oil films are partially blocking about 90% of the surfaces of the electrodes 20, 22, the capacitance due to the electrochemical double layer decreases about 1 order of magnitude, which does not practically affect impedance values measured at 20 kHz. Once the desired flow conditions were stabilized, the probe wiring was connected to the potentiostat and the impedance measurements were performed continuously for at least 1 minute using a sampling rate of approximately 0.5 s.

Isopar V®, a clear saturated paraffinic hydrocarbon of density 810 kg/m$^3$ and viscosity 0.009 Pa s at 25° C., was used as the oil phase. The water phase was the same 1 wt % NaCl solution used in the static experiments described above. The use of this highly conductive electrolyte may assist in preventing significant local conductivity changes when the solution comes in contact with the carbon steel test section, which easily corrodes releasing considerable amount of iron ions. The oil-water interfacial tension was measured as 0.049 N/m at 25° C.

Flow experiments were performed in horizontal condition at room temperature (~25° C.) using different mixture flow velocities from 0.7 m/s to 4 m/s and water cuts from 1% to 20%. In each experimental run, the polished test section 12 was first put in contact with oil at the highest available superficial velocity for the selected test water cut. The water was then injected and surface wetting was measured using the impedance probe 10. Subsequently, the oil superficial velocity was reduced to its next value maintaining the water cut, and the process was repeated until testing the lowest oil velocity. Once the experimental series was completed for the given water cut, the flow loop 30 was drained and the surface of the test section 12 was re-treated to test a different water cut.

Static wetting experiments of water-in-oil contact angles were also performed, using a goniometer, on the surface of a carbon steel specimen, prepared using the same procedure as for the test section 12. It was determined that the carbon steel surface behaves as hydrophilic after a few seconds, giving water-in-oil contact angles θ-60° (measured from the inside of the sessile water droplet).

Figure 6:
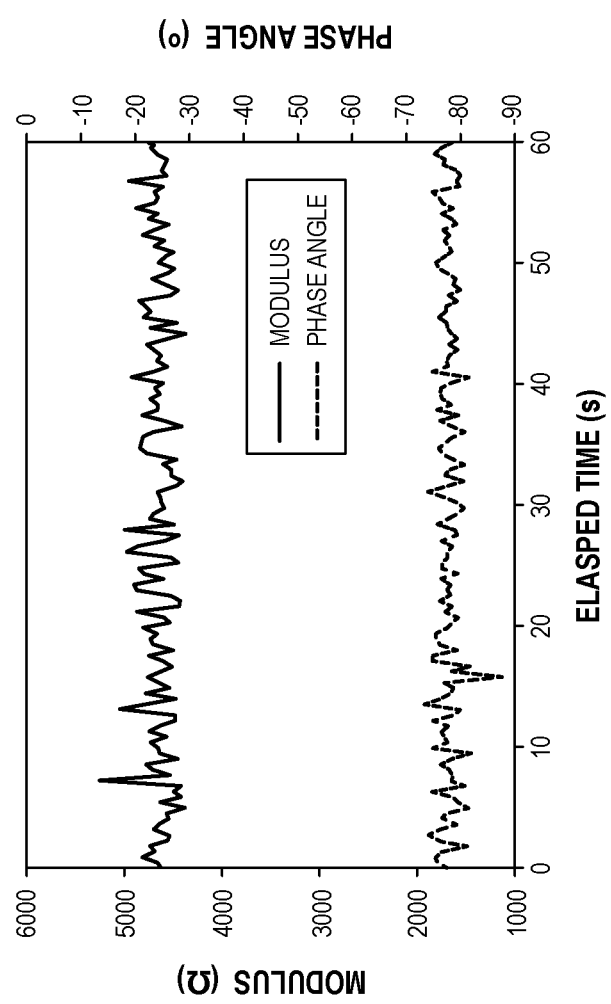
FIG. 6 is a plot of the impedance measured by the probe at 20 kHz as a function of time for oil only flow.

The response of the probe 10 to full oil wet conditions in this example will now be discussed. The measured impedance of the probe 10 and its wiring (used for remote operation) in oil only flow was the same as in air; its modulus and phase angle are illustrated in FIG. 6. A time-averaged modulus of about 4650Ω and phase angle of −78° were measured at 20 kHz, with maximum deviations in time of less than 15% for both values. The measured phase angle values were somewhat higher than −90° due to the slight inductive effect produced by the probe wiring. The total capacitance (Cp) of the probe 10 was measured as $1.7 \times 10^{-9}$ F.

Figure 7:
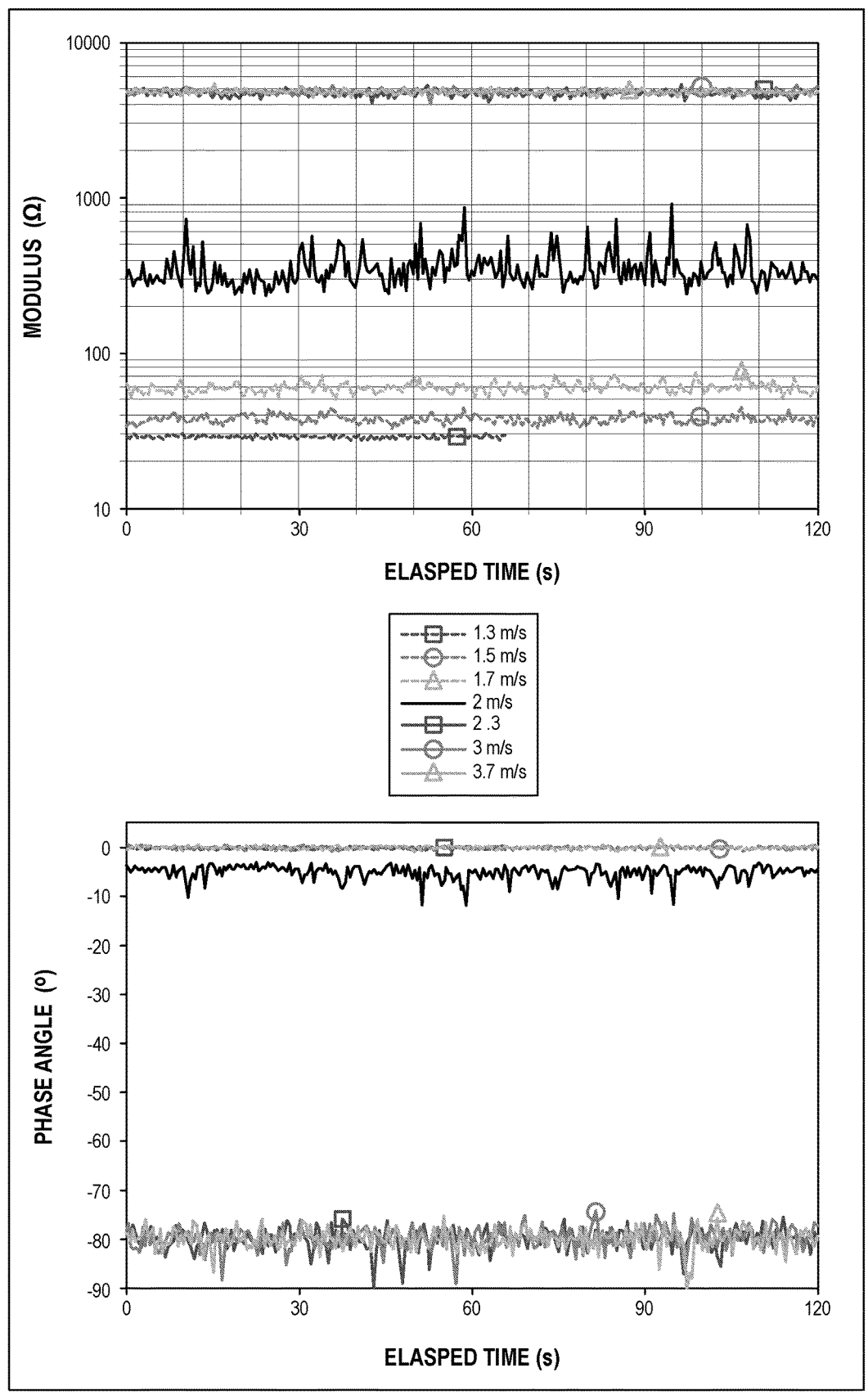
FIG. 7 is a plot of the impedance measured by the probe at 20 kHz as a function of time for horizontal oil-water flows with different mixture flow velocities and 3% water cut.

The response of the probe 10 in oil-water mixture flow will now be discussed. FIG. 7 shows examples of the impedance response with time for oil-water flows with different mixture flow velocities and a constant water cut (WC) of 3%. Each plotted value is the average of ten different measurements separated in time by about 1 wavelength period as provided by the intrinsic settings of the potentiostat. Thus, the measurements actually capture flow events with a lower effective frequency of about 1 kHz, which is more than enough to detect the transient behavior of water layers or rivulets passing on top of the employed probe 10.

From FIG. 7, it can be seen that for relatively large flow mixture velocities, for example 2.3 m/s or larger, the measured impedance shows capacitive behavior similar to when oil-only flow is measured (FIG. 6). This indicates that all the transported water is entrained and the pipe surface is only in contact with oil. For lower mixture velocities, the measured impedance modulus decreases and the phase angle increases, indicating the presence of water wetting the pipe wall. Lower impedance modulus and a phase angle approaching zero degrees (resistive behavior) is an indication that thicker water layers were present at the lower mixture velocities.

Figure 8:
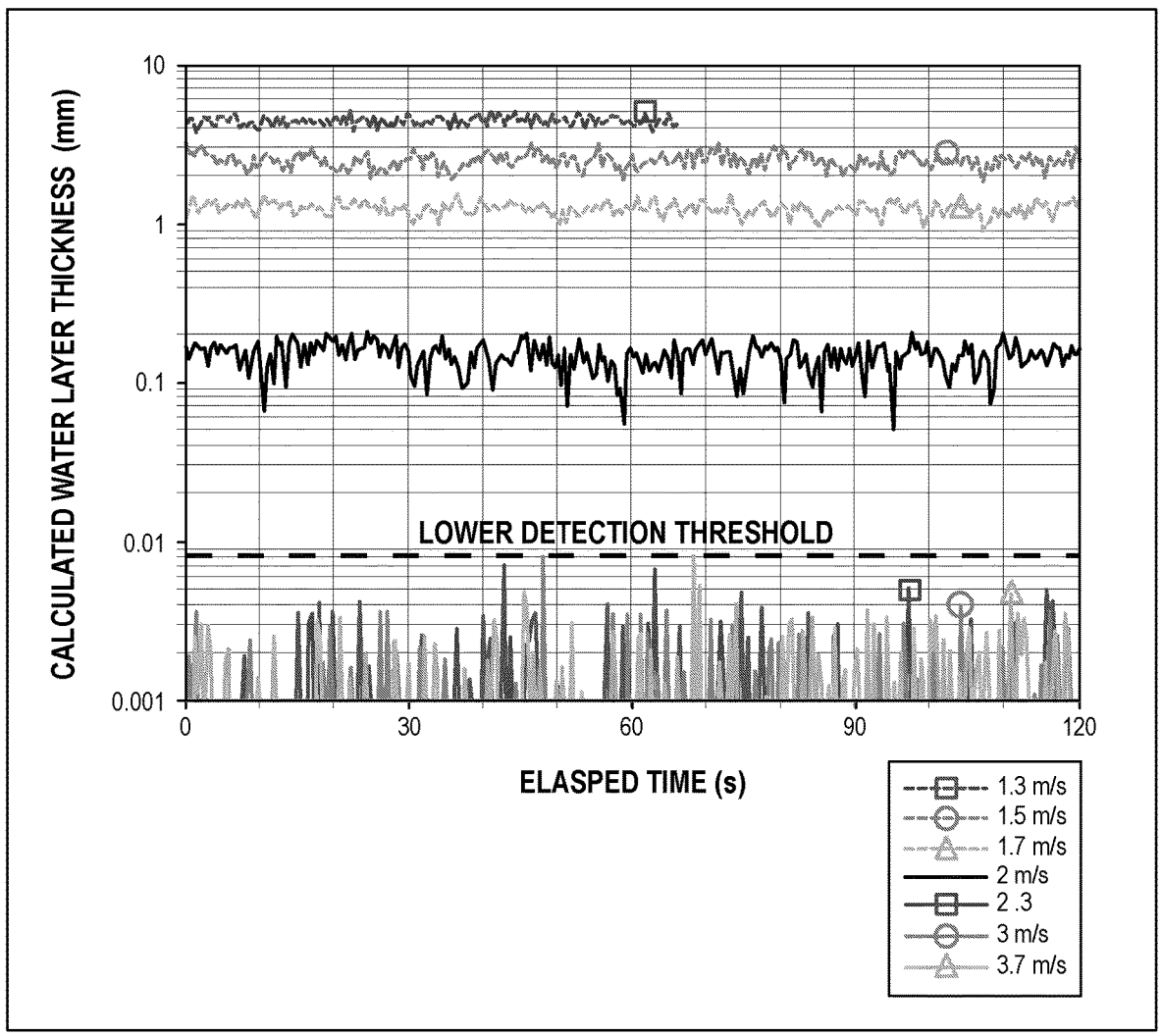
FIG. 8 is a plot of calculated water layer thickness as a function of time for horizontal oil-water flows with different mixture flow velocities and 3% water cut.

Estimations of the thickness of the water layers detected in FIG. 7 were done using equations (1)-(3) and (6), as shown in FIG. 8. The calculated values correspond to the average thickness of the water layer flowing on top of the concentric area between the probe electrodes 20, 22. Time-averaged water layer thickness values of approximately 0.13 mm, 1.2 mm, 2.5 mm and 4.3 mm were calculated for mixture velocities of 2 m/s, 1.7 m/s, 1.5 m/s and 1.3 m/s, respectively. In general, the water layers of smaller thickness display greater relative fluctuation with time. The thinner the segregated water layer is, the more unstable it becomes. This is due to the larger relative effect of mass gain via settling water droplets that incorporate into the film, or mass loss due to water entrained as droplets by the oil flow. It is also important to mention that water layer thickness values of the order of 0.1 mm can be somewhat biased due to height misalignment between the probe 10 and the surface of the test section 12. Local flow disturbances may affect the dimensional stability of water layers as thin as those measured at a mixture velocity of 2 m/s. It is also noteworthy that the measured impedance signal can be processed instantaneously after it is obtained. This allows characterization of water layer thicknesses not only in situ but also in terms of how they evolve in real time. The smallest detectable water layer thickness depends on the intrinsic impedance of the probe 10, the conductivity of the water, and the noise level of the measured electrical signal (which may be inherent to the quality of the electronic measurement device and wiring). For this example, the detection threshold is about 0.008 mm (indicated with a dashed line in FIG. 8 for the 2.3 m/s, 3 m/s and 3.7 m/s mixture velocity series), which corresponds to the lowest fluctuating value of impedance measured in the absence of water. However, water layers with average thicknesses at least as low as 0.003 mm may still be detected with the probe 10. It is worth mentioning that the minimum detectable water layer thickness can be reduced regardless of the intrinsic electrical noise of the measurement by increasing either the water conductivity or the impedance of the probe 10 (lower capacitance), which is a parameter that can be engineered jointly with the geometry of the electrodes 20, 22 to optimize the useful measurement range of the probe 10.

In order to illustrate the ability of the impedance measurements to sense water or oil wetting, experiments with constant flow characteristics were run and subsequent visual internal inspections of the test section 12 performed. Each experiment started with a freshly polished surface exposed to a consistent oil-water flow regime with certain characteristics (e.g., mixture velocity of 1.7 m/s and 3% water cut) for 30 minutes. The water supply was then shut off and oil solely circulated for several minutes. This flow was subsequently stopped and the flow loop 30 drained and disassembled, allowing internal inspection of the test section 12. FIGS. 9B-9C show images representative of the internal surface of the carbon steel pipe section 12 after the tests. For the 1.7 m/s mixture velocity (FIG. 9B), evidence of a well-developed water path at the pipe bottom is clearly observed due to the presence of a corrosion product, which was absent in the areas of the pipe wall that remained oil wet. In the case of the 3.7 m/s mixture velocity (FIG. 9C), the surfaces of the test section 12 did not show visible evidence of a water path intercepting the location of the impedance probe 10. Moreover, only traces of two minor water trails were found at the sides near the pipe bottom. These did not extend along the entire length of the test section 12 and could have been produced by small flow disruptions produced by slight protrusions of the gasket at the flange joint upstream of the test section 12. Visual inspection tests proved to be in line with the measurements by the impedance probe 10 regarding the presence or absence of segregated water layers in all test cases.

Figure 10:
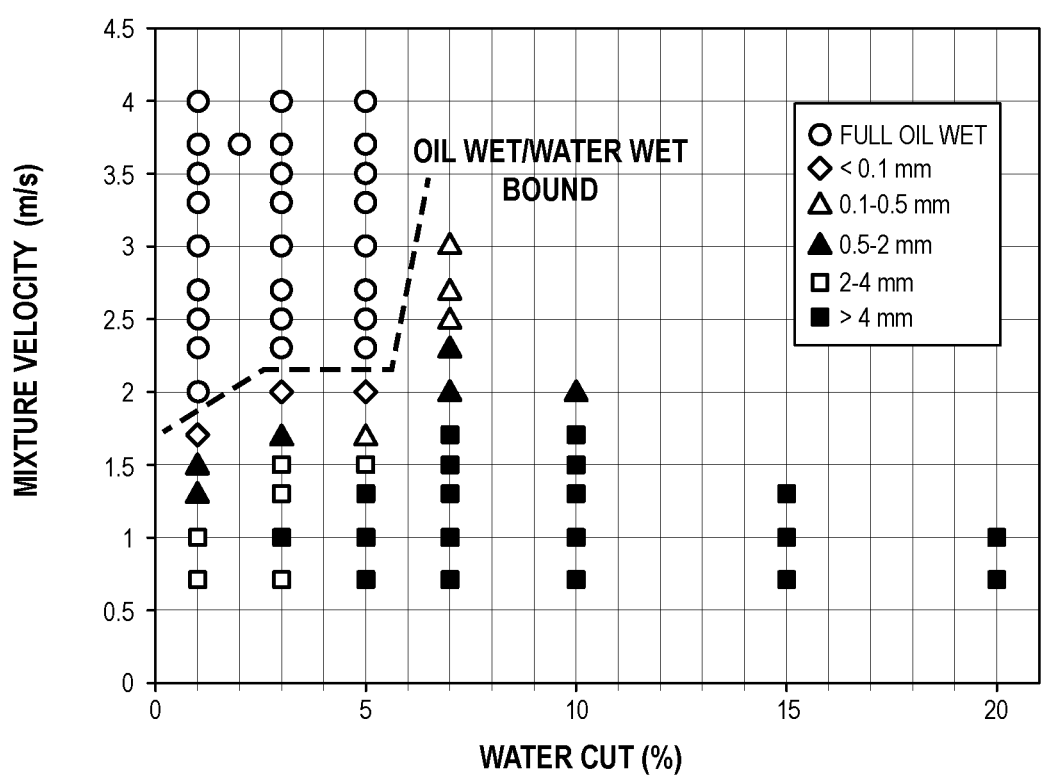
FIG. 10 is a map of phase-wetting regime and time-averaged water layer thickness at the pipe bottom in horizontal oil-water flow in the carbon steel pipe of FIG. 4 obtained using the probe.

FIG. 10 illustrates a map of a phase-wetting regime constructed using the results obtained from the impedance probe 10 in this example. The map shows areas with no data at the upper right corner due to the limitation of the flow rig to deliver larger water flow rates. The plotted phase-wetting regimes are based on the results of at least 2 independent experimental runs and characterized as "full oil wet" (circles), where only oil was detected, or water wet where water was detected with different layer thicknesses; the data is arranged in ranges to illustrate their variation with flow conditions (e.g., hollow triangles indicate average water layer thicknesses between 0.1 mm and 0.5 mm). The time-averaged water layer thicknesses were calculated from the impedance data via equations (1)-(3) and (6). In general, the larger the water cut, the higher mixture velocity required to avoid water separating from a dispersed condition and generating streams or layers at the pipe bottom. For example, full oil wet to water wet transition happens at mixture velocities of about 1.7 m/s and 2 m/s for water cuts of 1% and 5%, respectively. Moreover, full oil wet regime is not observed even at mixture velocities as large as 3 m/s for water cuts larger than 5%. Instead, very thin water layers (e.g., having a thickness less than 0.5 mm) are detected at the pipe bottom. This behavior may be related to a hydrophilic nature of the surface of the carbon steel test section 12. Even in very turbulent flow conditions, where hydrodynamic dispersive forces of the continuous phase are significant, some dispersed water droplets will tend to hit the bottom pipe wall due to the gravity action. These droplet-wall collisions are not frequent at low droplet concentrations, but at higher droplet concentrations can occur at significant rates. Colliding water droplets are prone to stick onto the hydrophilic carbon steel surface subsequently forming thin water layers that do not grow much in thickness due to the shearing action of the continuous phase flow. Hydrophobic internal pipe walls (e.g., PVC pipes) might not show the formation of thin water layers at relatively high oil velocities and moderate water volume fractions since colliding droplets are less prone to stick onto such pipe surfaces.

Regarding the performance of the high frequency impedance probe 10 used in this example, it is noteworthy that when the measured amounts of water are very small (water layer thickness of the order of about 0.1 mm or lower), water is more likely to wet as tiny rivulets instead of a thin film covering the whole exposed surface of the probe 10. Accurate characterization of water layer thickness may occur when the surface of the impedance probe 10 becomes completely covered by the conductive layer. Incomplete coverage may lead to underestimation of the real layer thickness. This may be addressed by using a probe 10 of smaller dimensions, which may result in sacrificing depth measurement range. Arrangements of flush-mounted probes 10 distributed along the circumference of a pipe 14 can also be used to study phase wetting in conditions in which water can be transported to the side or top walls of the pipe 14 (e.g., in three-phase oil-water-gas flow). While the accuracy of water layer thickness characterization using high frequency impedance measurements on the flush mounted probe 10 and signal processing based on the theoretical probe response has only been discussed above in static conditions, the water layer thickness results for the dynamic conditions of this example are believed to be accurate so long as the geometrical limitations discussed above (e.g., layer not covering the whole surface of the probe 10) are accounted for.

Given the results of this example, the used high frequency impedance probe 10 and measurement setup provides a method of obtaining phase wetting and water layer thickness information that can then be used to check and/or develop flow models to predict fully dispersed water-in-oil flow boundaries and water wetting phenomena. Additionally, water layer thickness data can be used to estimate the flow rate of the segregated water and to perform better corrosion risk assessment of industrial facilities via mechanistic modeling, such as if the chemical composition of the water (e.g., pH, dissolved minerals and organics), pressure and temperature are known.

Example 2

Figure 11:
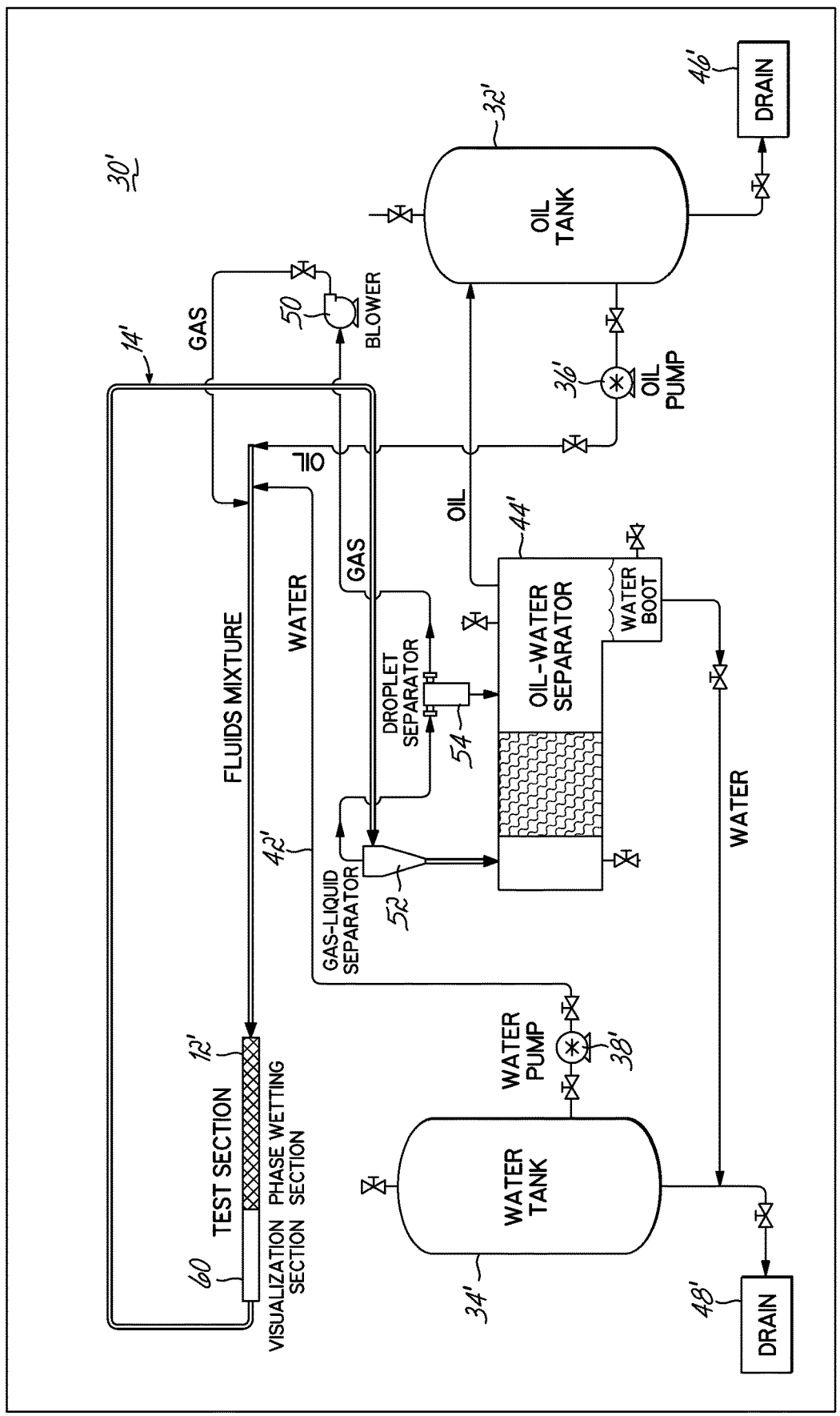
FIG. 11 is a schematic view of a flow loop used for oil-water-gas flow tests in accordance with another aspect of the present invention.

In this example, wherein like numerals represent like features, the flow loop 30' is constructed from 0.1 m ID pipe and consists of two main legs of 15 m length connected with two bends of 90 degrees, as seen in the schematic in FIG. 11. The main line 14' (upstream leg) is used for the phase wetting tests and is equipped with a carbon steel test section 12' with impedance probes 10, 10' and a transparent section for flow visualization, both located close to the end of the leg. The main legs 14' of the flow loop 30' are mounted on a steel structure (not shown) that allows inclination from 0 degrees (horizontal) to 90 degrees (vertical) positions.

The oil flow is fed directly into the main line 14' while the water is directed from the water storage tank 34' through a 0.05 m ID PVC pipe 42' and connected to the main line 14' via a T-section. The gas stream is introduced into the main line 14' via a 0.1 m ID 45-degree elbow. The mixing of the fluid streams (oil, water and gas) starts at the beginning of the main upstream line 14' of the flow loop 30' and develops further downstream through a stainless steel pipe 14' until reaching the phase wetting test section 12', located at about 140 pipe diameters from the water and gas injection point. The two legs of the flow loop 30' are connected with the rest of the system through a 0.1 m ID and 3 m long flexible hose, which allows for rig inclination.

The liquids were pumped into the main flow line 14' by positive displacement pumps 36', 38' with variable speed electric motors. Liquid flow rates were monitored by turbine and paddle wheel flow meters (not shown), connected to a computer for data acquisition and recording. The gas stream was circulated to the main line 14' by a positive displacement lobe-type blower 50. The gas velocity was measured using hot wire anemometry.

Upon exiting the main line 14', the flow stream is directed to the separation unit, which includes a gas-liquid separator 52 with droplet separator 54 and an oil-water separator 44'. The separated oil and water streams are returned to their respective storage tanks 32', 34', made of stainless steel with a capacity of 1.2 m³ each, while dry gas is recirculated by the blower 50.

Phase wetting tests were carried out in a 0.1 m ID and 1.8 m long carbon steel pipe section 12', as shown in FIGS. 12A and 12B. Phase wetting regime and thickness of developed water layers were measured using concentric two-electrode high frequency impedance probes 10, 10'. In particular, a single large probe 10 with an inner carbon steel electrode 22 having a radius $r_i$ of approximately 6.2 mm and an outer stainless steel electrode 20 having a radius $r_0$ of approximately 12.5 mm was used flush-mounted at the pipe bottom, where water is most likely to segregate. In this example, the probe 10 is positioned at a distance D1 of approximately 0.25 m from the outlet end of the section 12'. This configuration was similar to that of the first example used to measure phase wetting and water layer thickness in two-phase oil-water flow. In addition, an array of 16 flush mounted probes 10' of similar design and smaller dimensions were staggered around the pipe circumference to detect the presence of water at the top and side pipe walls. In particular, the probes 10' each had two concentric stainless steel electrodes, including an inner stainless steel electrode (not shown) having a radius $r_i$ of 1.5 mm and an outer stainless steel electrode (not shown) having a radius $r_o$ of approximately 4.7 mm. In this example, the array of probes 10' is divided into two annular portions, wherein the probes 10' of each annular portion are angularly displaced from each other by an angle α of approximately 45° about the circumference of the pipe 12', and wherein a centerline between the two annular portions is positioned at a distance D2 of approximately 0.8 m from the inlet end of the section 12'.

All the probes 10, 10' were operated separately with an AC voltage of 10 mV rms and a frequency of 20 kHz using a Gamry REF 600® potentiostat with a computer interface. Once the desired flow conditions were stabilized, the probe wiring was connected to the potentiostat and the impedance measurements were performed continuously for at least 2 minutes using a sampling period of approximately 0.5 seconds. The presence of water layers in contact with each probe 10, 10', and their thickness, was determined from the measured impedance values (modulus and phase angle) in relation to the theoretical response of each probe 10, 10' and the electrical conductivity of the water phase, in a manner similar to that discussed above.

Before each set of experimental runs, where about 6 flow conditions were tested, the internal surface of the test section 12' was polished using a rotating flexible abrasive tool (180 grit) with deionized water as the polishing fluid. The surface was then washed with deionized water and isopropanol, then dried with a clean cloth.

Static wetting experiments of water-in-oil contact angles were also performed, using a goniometer, on the surface of a carbon steel specimen, prepared using the same procedure as for the test section 12'. It was determined that the carbon steel surface exhibits hydrophilicity after some seconds, giving water-in-oil contact angles of about 60° (measured from the inside of the sessile water droplet).

A clear acrylic section 60 was located just downstream of the carbon steel test section 12' to allow visualization of the developed flow patterns, recorded as pictures and videos using a high-resolution digital camera. When slug flow was present, the average frequency between liquid slugs was measured from the recorded videos.

In this example, Isopar V®, a clear saturated paraffinic hydrocarbon, was used as the oil phase. The water phase was 1 wt. % NaCl solution prepared from deionized water. Air was used as the gas phase. The properties of the test fluids are listed in Table 1.

The use of a highly conductive electrolyte as water phase (1.76 S/m) helps preventing significant local conductivity changes when the solution comes in contact with the carbon steel test section 12', which may corrode and release iron ions.

The oil-water inversion point is indicated as water phase volumetric concentration. It was measured in a stirred vessel using two-electrode high frequency impedance measurements.

TABLE 1

List of properties of the test fluids (values at 25° C.)

| Property | Oil | Water | Gas |
|---|---|---|---|
| Density (kg/m$^3$) | 810 | 1005 | 1.12 |
| Dynamic viscosity (Pa · s) | 0.01 | 0.001 | 17 × 10$^{-6}$ |
| Surface tension (N/m) | 0.03 | 0.072 | — |
| Oil-water interfacial tension (N/m) | 0.049 | | N/A |
| Oil-water inversion point (%) | 25 | | N/A |

The test flow conditions will now be described for this example. Flow experiments were performed in horizontal condition at room temperature (~25° C.) and atmospheric pressure using different superficial liquid velocities, superficial gas velocities and water cuts. Table 2 lists the conditions used in the flow tests.

TABLE 2

Conditions used in the flow tests

| Parameter | Value |
|---|---|
| Superficial liquid (oil + water) velocity (m/s) | 0.1-1.5 |
| Superficial gas velocity (m/s) | 1-20 |
| Water cut (%) | 1-10 |

The maximum uncertainty in the oil superficial velocity and the water superficial velocity values was 10% and 15%, respectively. The maximum uncertainty in the superficial gas velocity was 15%, for values lower than 10 m/s, and 20% for larger velocities.

Each flow condition was repeated at least twice, showing good reproducibility. The experimental data shown in below are the average of at least two independent runs. Once a flow condition was set, it was run for about 10 minutes before measuring phase wetting regime and recording flow pattern.

Figure 13A:
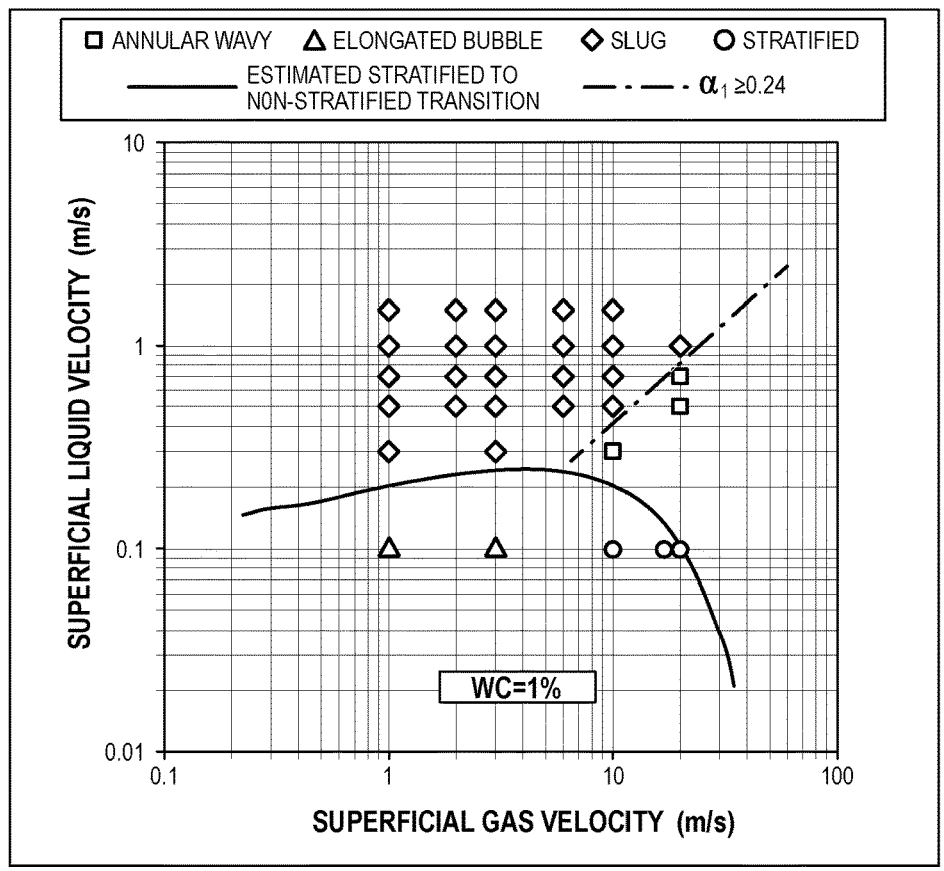
FIGS. 13A-13C are plots of gas-liquid flow patterns found for horizontal oil-water-gas flow with different water cuts.
Figure 13B:
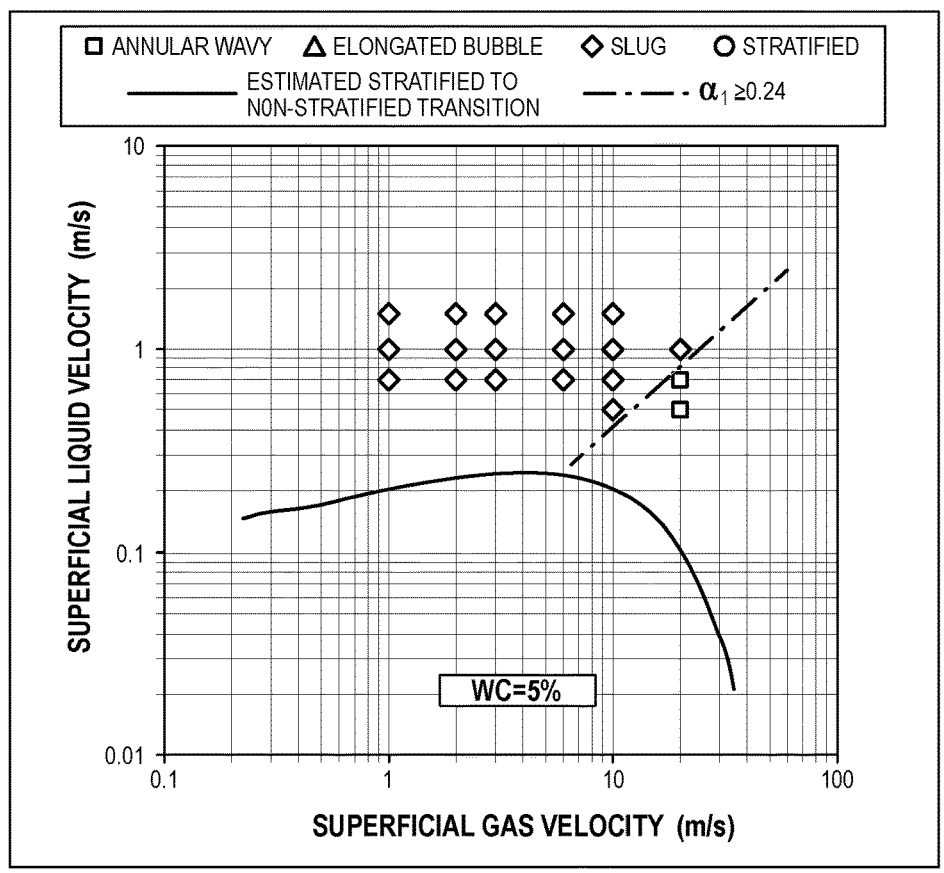
Figure 13C:
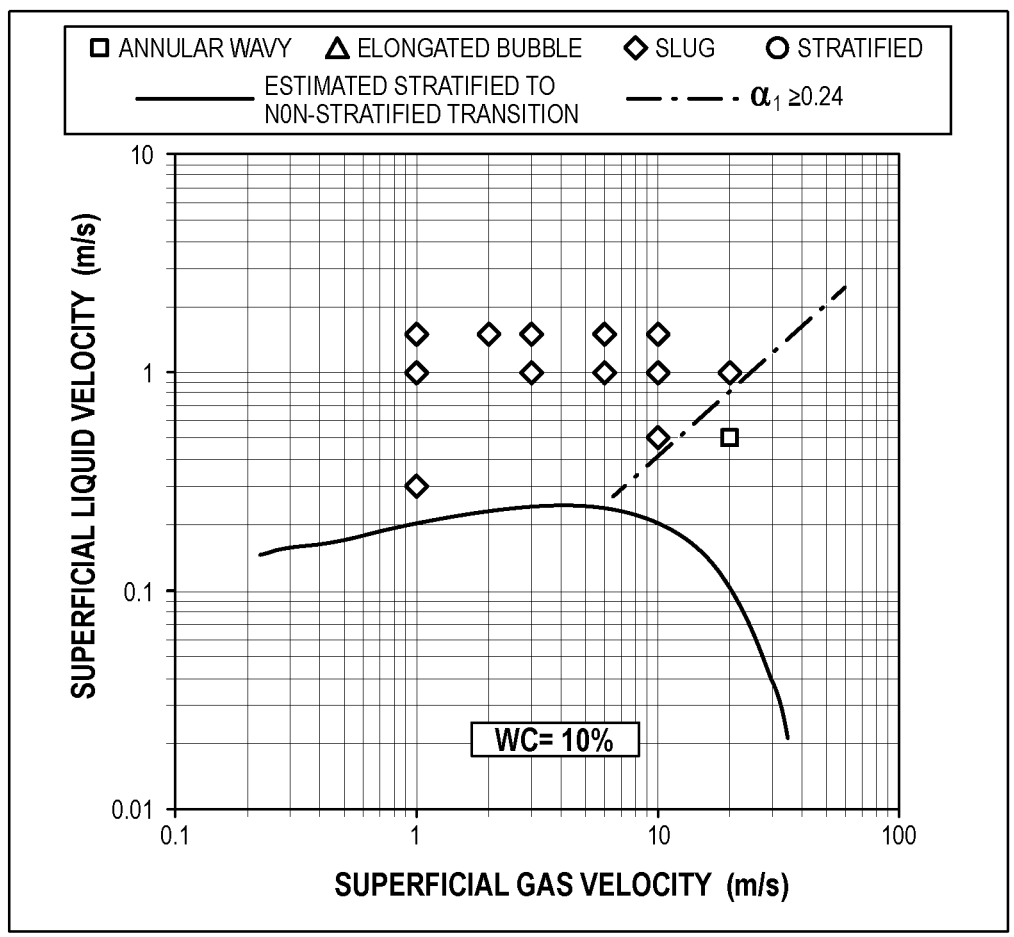
Figure 14:
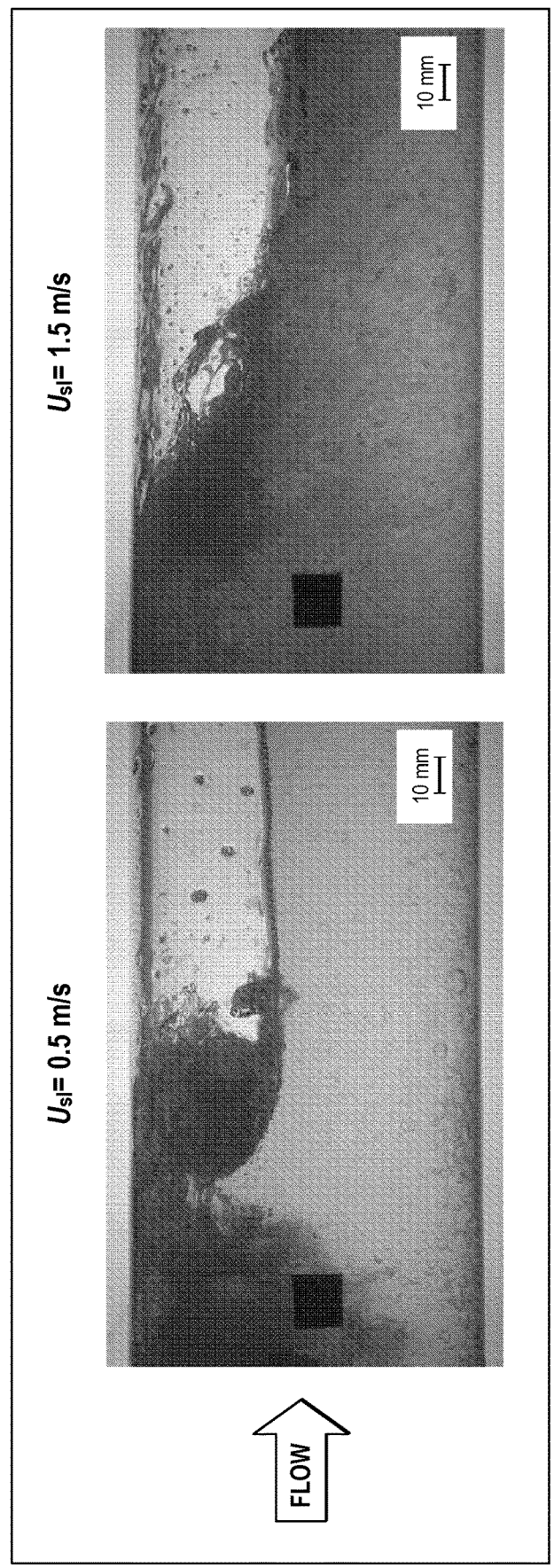
FIG. 14 is a pair of photographs depicting examples of slug flow patterns observed from the side of the clear section of the flow loop of FIG. 11, with a superficial gas velocity ($u_{sg}$) of 1 m/s and 1% water cut.

The characterization of gas-liquid flow patterns in this example will now be discussed. FIGS. 13A-13C show the gas-liquid flow patterns observed for the different used superficial liquid and gas velocities and water cuts. Slug flow is predominantly found in the range of superficial liquid velocities ($u_{sl}$) from 0.3 m/s to 1.5 m/s and superficial liquid velocities ($u_{sg}$) from 1 m/s to 10 m/s, which is somewhat in line with the estimated stratified to non-stratified modeled transition (solid line). A transition to an annular wavy flow pattern is seen at $u_{sg}$ values of 20 m/s and $u_{sl}$ values lower than 1 m/s, or $u_{sg}$ values of 10 m/s and $u_{sl}$ values lower than 0.5 m/s, in agreement with the criterion of liquid holdup (α1) larger or equal to 0.24 for intermittent flow (dash-dot line). Elongated bubble and stratified flow patterns are found for a superficial liquid velocity of 0.1 m/s. Increasing the water cut from 1% to 10% does not alter gas-liquid flow patterns. FIG. 14 shows examples of slug flow patterns observed from the side of the pipe clear section 60 located downstream of the carbon steel test section 12' for $u_{sg}$=1 m/s and 1% water cut and $u_{sl}$ values of 0.5 m/s and 1.5 m/s. It can be seen that for the lower superficial liquid velocity (0.5 m/s), water is distributed mostly at the pipe bottom semi-dispersed as water globules. For the larger superficial liquid velocity (1.5 m/s), the water phase is distributed more uniformly in the liquid mixture.

Figure 15:
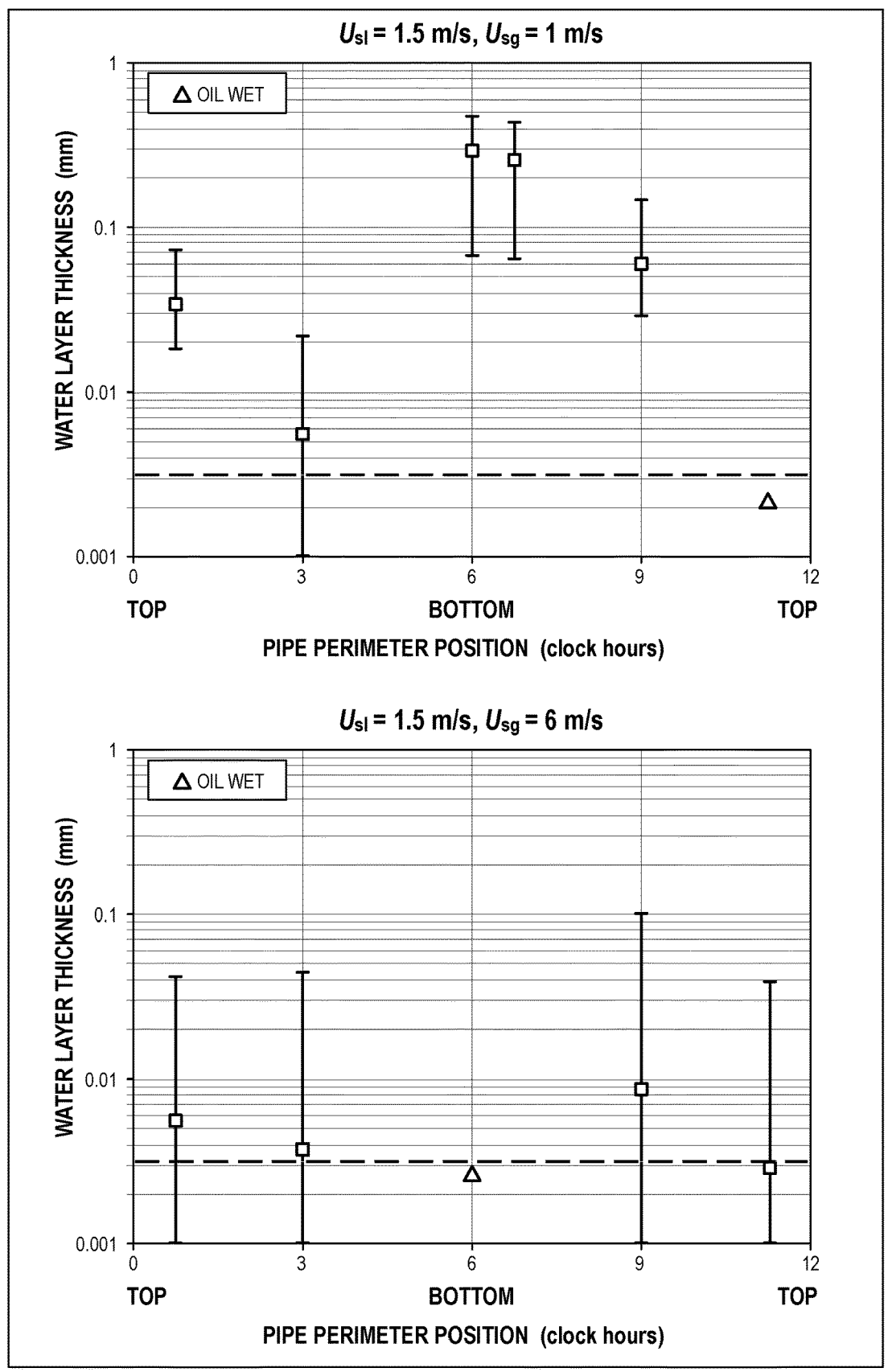
FIG. 15 is a pair of plots depicting examples of time-averaged water layer thickness estimated from high frequency impedance measurements around the pipe circumference in three-phase horizontal slug flow with 5% water cut and different superficial gas velocities.
Figure 16:
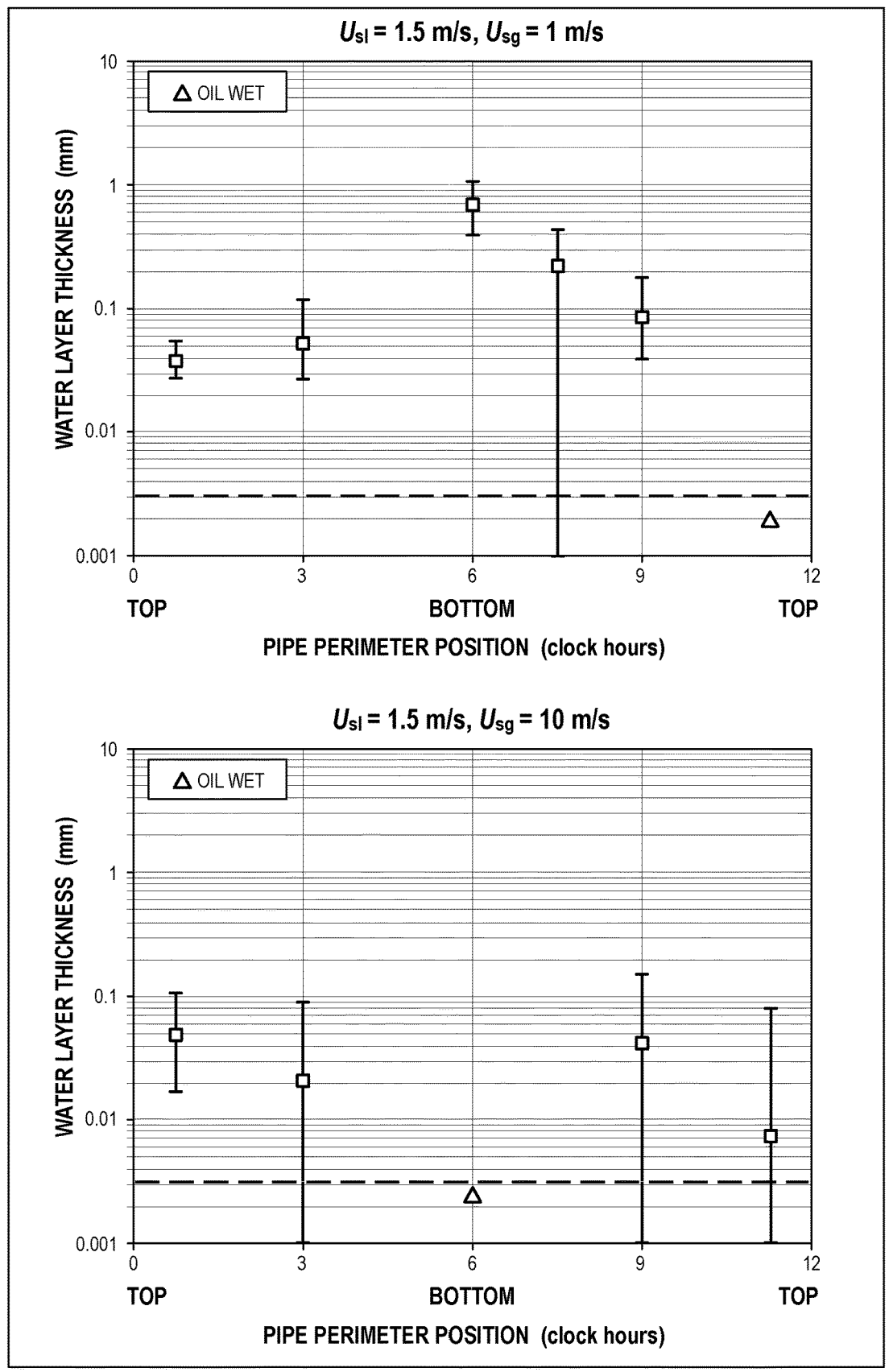
FIG. 16 is a pair of plots depicting examples of time-averaged water layer thickness estimated from high frequency impedance measurements around the pipe circumference in three-phase horizontal slug flow with 10% water cut and different superficial gas velocities.

The characterization of phase wetting and water layer thickness in this example will now be discussed. Turning first to water layers developed around the pipe circumference, FIGS. 15 and 16 show examples of time-averaged water layer thickness estimated from high frequency impedance measurements on some of the small probes 10' located around the pipe test section 12' in three-phase slug flow with 5% and 10% water cut, respectively. Error bars show maximum and minimum values. In this example, the lowest water layer thickness which may be detected is about 0.003 mm on average. No evidence of water or corrosion was found for impedance measurements equivalent to water layer thicknesses lower than this value as discussed above and, therefore, estimated thicknesses below 0.003 mm (dashed line) are considered as oil wet (positions marked with triangles). It can be seen that for relatively low gas superficial velocity ($u_s i$=1 m/s), water drops out from dispersion due to gravity forming water layers that have maximum thickness at the pipe bottom (e.g., at the 6 o'clock position). For example, average thicknesses of ~0.3 mm and ~0.7 mm are measured for 5% and 10% water cut, respectively. It is worth noting that thin water films from 0.01 m to 0.1 mm thickness are also detected at the upper half of the pipe 12'. The occurrence and thickness of these thin films are irregular along the upper pipe perimeter.

Increasing superficial gas velocity (e.g., 6 m/s and 10 m/s for 5% and 10% water cut, respectively) water droplets can be effectively entrained by the oil flow as no water layer is detected at the pipe bottom. However, thin water films with average thickness smaller than 0.1 mm still form at the upper half of the pipe 12', especially for the largest water cut of 10%.

Figure 17:
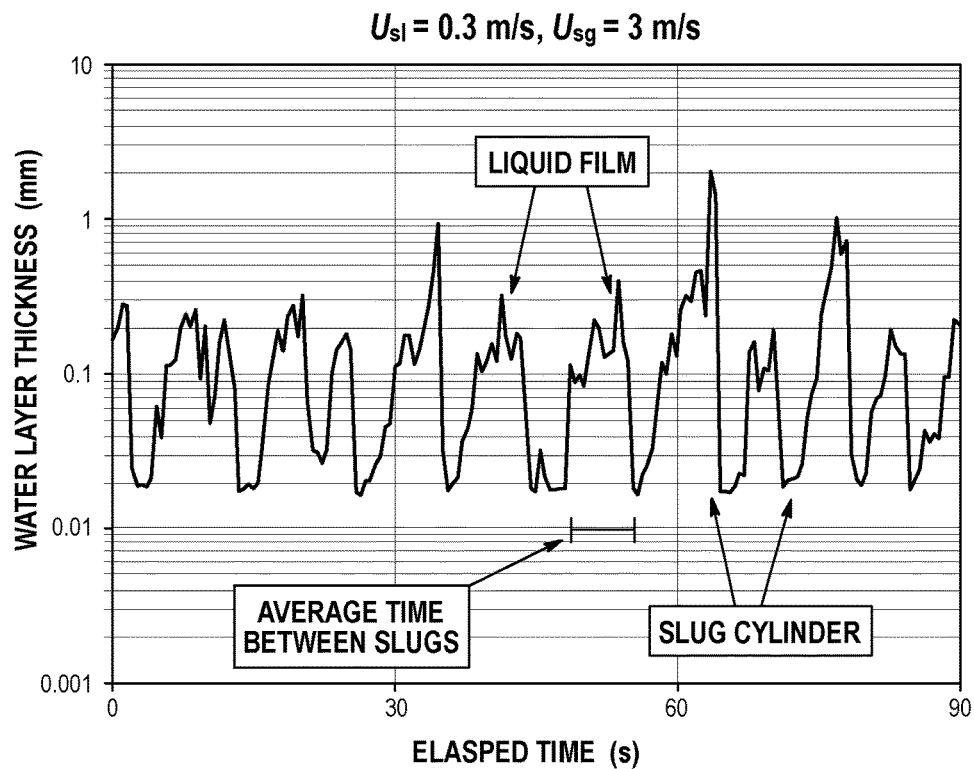
FIG. 17 is a plot depicting an example of water layer thickness measured at the pipe bottom as a function of time in three-phase horizontal slug flow with 1% water cut.

The thickness of the water layer developed at the pipe walls can vary significantly with time as inferred from the error bars in FIGS. 15 and 16. This is mainly related to the intermittent nature of slug flow. FIG. 17 shows a clear example where the pattern of variation in time of the water layer thickness measured at the pipe bottom coincides with the average measured time between slugs, which is about 6 seconds for this flow condition. Water segregates at the liquid film region and then is partially or totally swept off and entrained by the passage of the liquid slugs. These effects can lead to either intermittent water wet or intermittent oil wet regimes.

Figure 18:
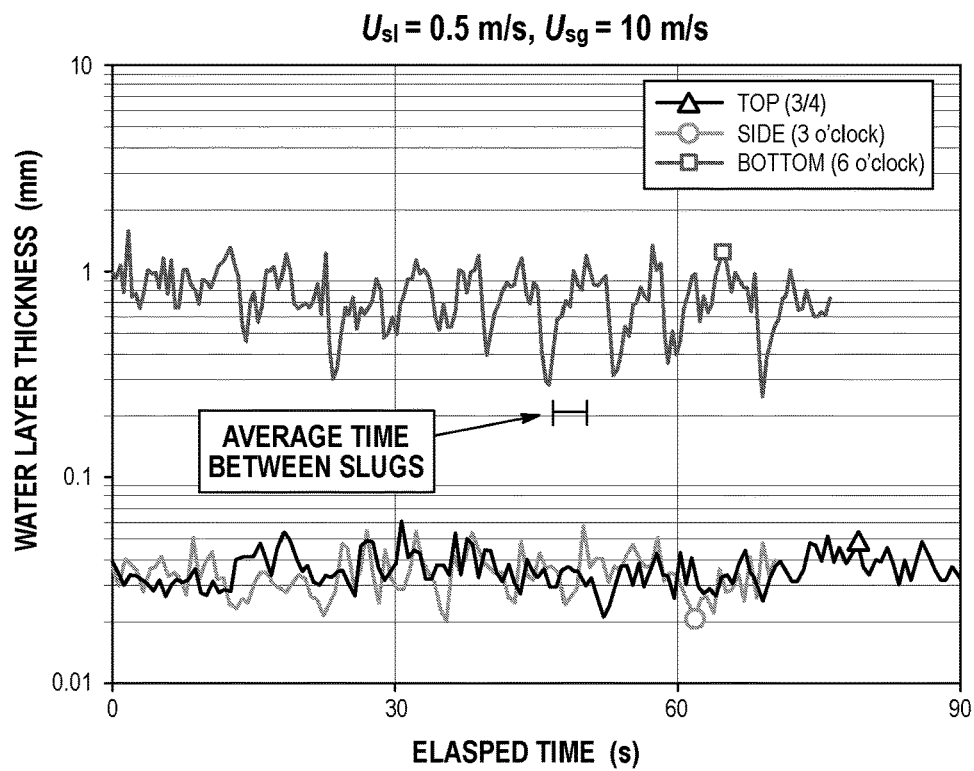
FIG. 18 is a plot depicting an example of water layer thickness measured at the pipe circumference as a function of time in three-phase horizontal slug flow with 10% water cut.
Figure 19A:
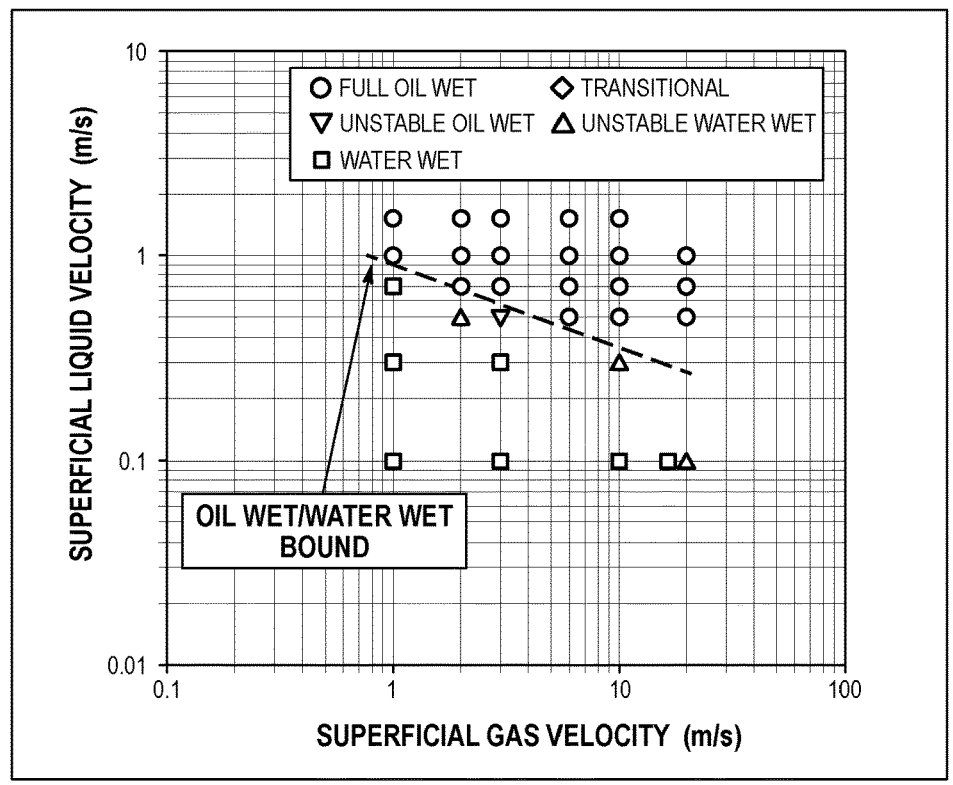
FIGS. 19A and 19B are plots depicting phase wetting regime (19A) and time-averaged water layer thickness (19B) measured at the bottom of the carbon steel pipe of the flow loop of FIG. 11 for different superficial gas and liquid velocities in three-phase horizontal slug flow with 1% water cut.
Figure 19B:
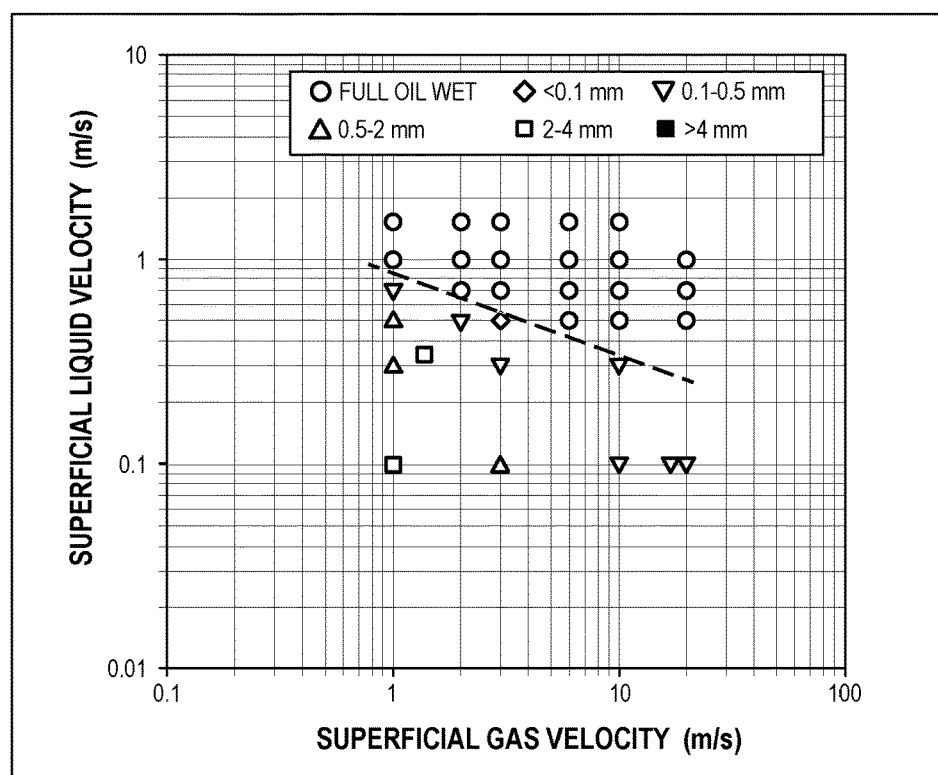
Figure 20A:
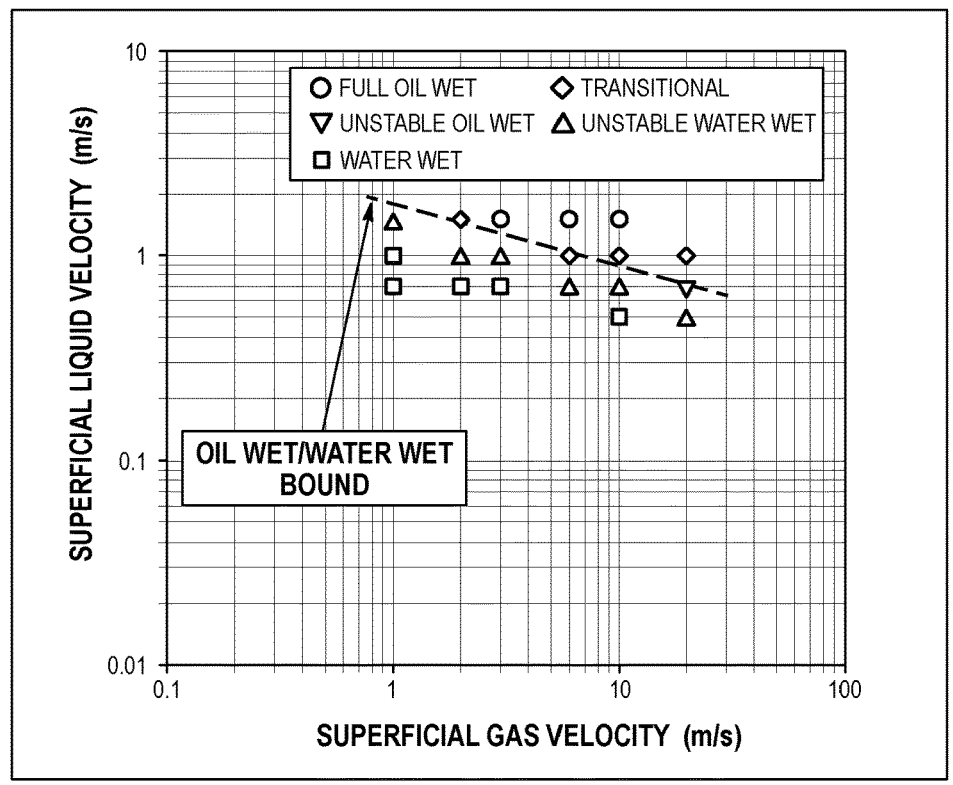
FIGS. 20A and 20B are plots depicting phase wetting regime (20A) and time-averaged water layer thickness (20B) measured at the bottom of the carbon steel pipe of the flow loop of FIG. 11 for different superficial gas and liquid velocities in three-phase horizontal slug flow with 5% water cut.
Figure 20B:
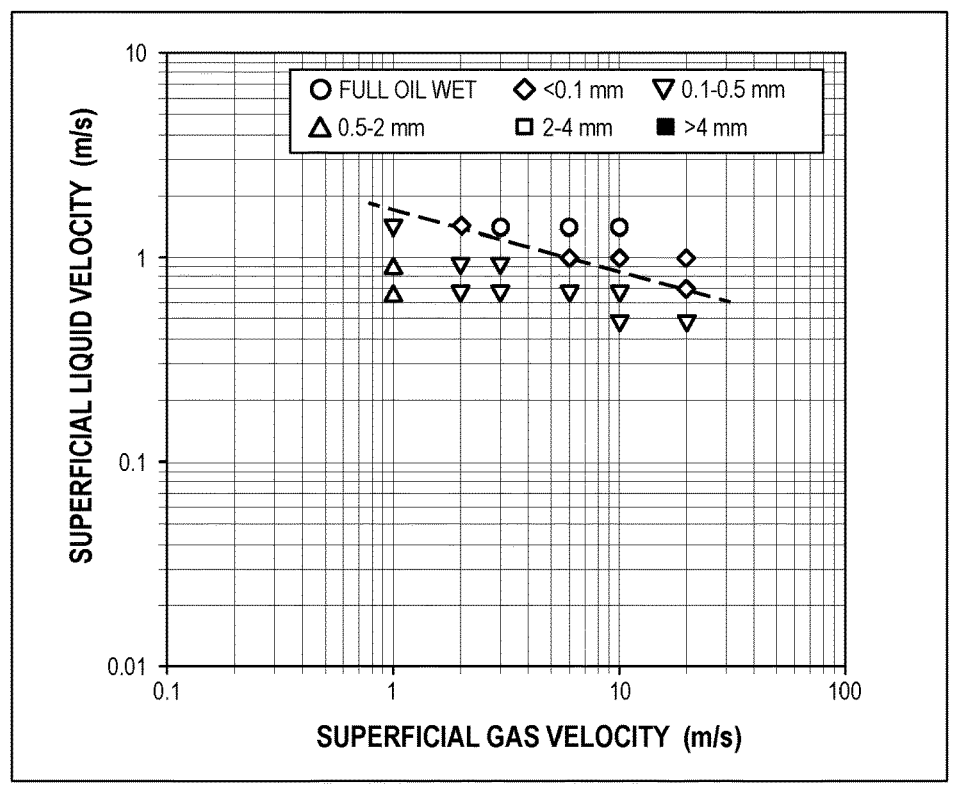
Figure 21A:
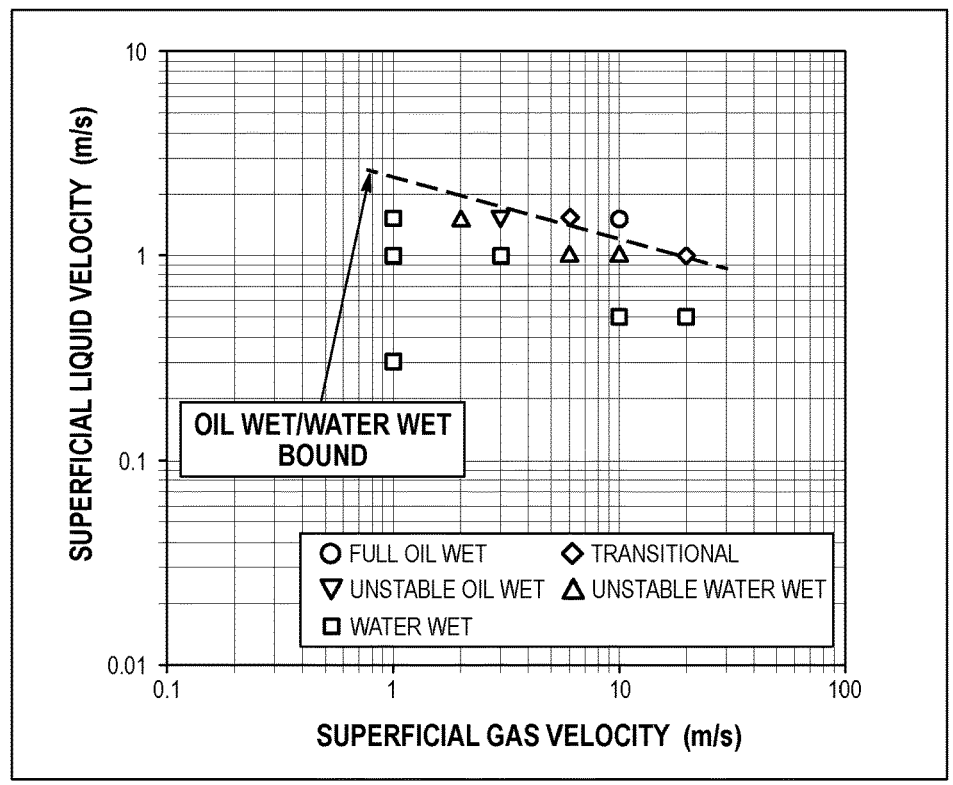
FIGS. 21A and 21B are plots depicting phase wetting regime (21A) and time-averaged water layer thickness (21B) measured at the bottom of the carbon steel pipe of the flow loop of FIG. 11 for different superficial gas and liquid velocities in three-phase horizontal slug flow with 10% water cut.
Figure 21B:
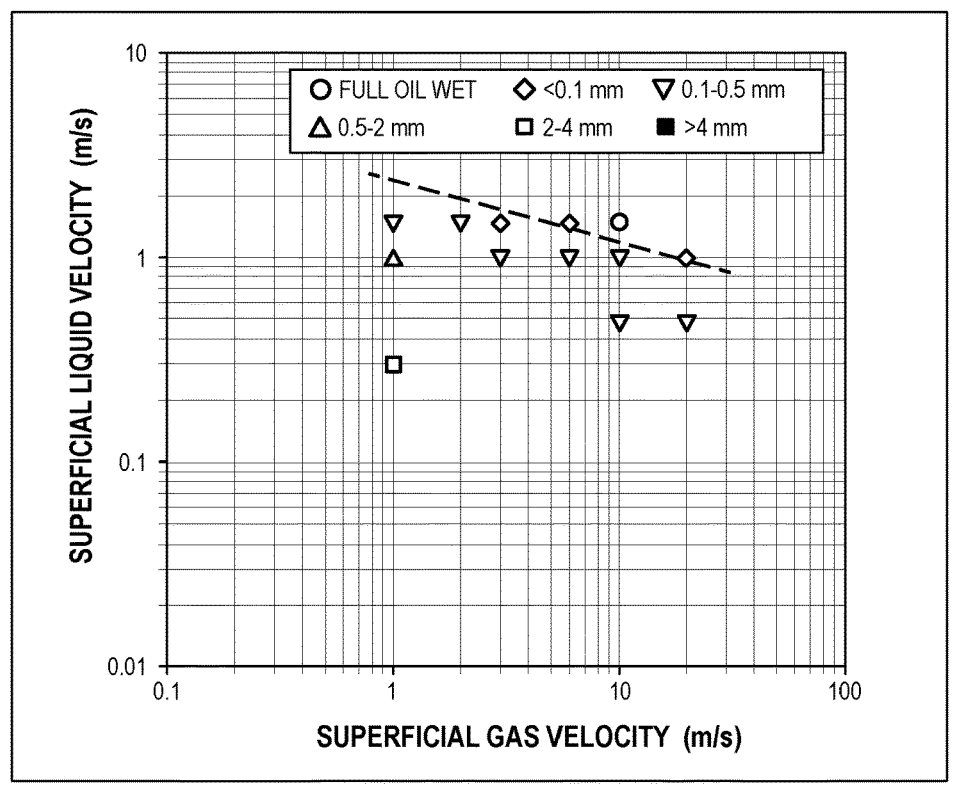

FIG. 18 shows an example of water layer thickness as a function of time measured at different locations of the pipe circumference. Similarly, as also seen in FIG. 17, the variation of the water layer thickness monitored at the pipe bottom somewhat correlates with the average measured time between slugs (~3.5 seconds). On the other hand, it is difficult to infer if the water layer thickness monitored at the top and side of the pipe vary in accordance with the average period between slugs. The formation of water films at the upper half of the pipe would be related to the sporadic deposition of dispersed water droplets that rapidly come in contact with the pipe wall when slugs are developed. In this case, droplet deposition may not always happen when each slug passes, since it depends on variable factors such as the size, velocity and impact angle of the impinging water droplets. The combination of these factors can produce quite different effects when water droplets impact the top and side pipe walls, such as due to deposition or rebound. Moreover, oil films are commonly found attached to the upper pipe surface between slugs (as seen in FIG. 14), and drip by gravity from the top to the side pipe walls. These films can alter the wettability of the pipe surface (e.g., turning it hydrophobic) as well as damp the impact of contacting water droplets ("cushioning"); both effects tend to reduce droplet deposition. The thickness of the thin water films monitored at the upper half of the pipe 12' tends to increase with water cut. This is in line with the fact that more water droplets per unit of volume of liquid mixture are available to be deposited onto the pipe surface.

In general, two types of water wetting scenarios are found in three-phase slug flow in carbon steel pipe 12'. The first is the formation of water layers at the pipe bottom due to gravity, such as by deposition and agglomeration and coalescence of sinking water droplets at the pipe bottom. The second is the sporadic deposition of water droplets at the upper half of the pipe 12' due to rapid contact of the liquid mixture with the pipe surface when slugs are formed.

The latter may not be considered as a serious problem since, in general, natural components of crude oil (e.g., organic acids) can alter carbon steel surface making it hydrophobic. In this context, droplets would not easily deposit at the upper pipe wall preventing the formation of water films. Moreover, if very thin water films (smaller than 0.1 mm thickness) are formed, they might be rapidly saturated with, e.g., ferrous ions from the occurring corrosion processes due to their large surface/volume ratio and limited replenishment promoting the formation of protective corrosion product layers. On the other hand, water drop-out due to gravity is the most serious concern since water accumulates predominantly at the pipe bottom.

Turning now to phase wetting regimes and water layer thickness at the pipe bottom, all the surface wetting and water layer thickness maps described below are based on the information obtained using the single large high frequency impedance probe 10 located at the pipe bottom. This larger probe 10 senses a wider area than the smaller probes 10'; thus, it may be more suitable for characterizing the average phase wetting behavior at the bottom of the pipe 12'.

As described above, the water streams detected in contact with the bottom pipe wall showed intermittent variation of their thickness with time. Moreover, in some cases the occurrence of free water at the pipe wall was alternating. This led to a wide categorization of the measured phase wetting regimes, which are described as follows. "Full oil wet" refers to when water is not detected or it is detected less than 30% of the measuring time with layer thickness lower than 0.1 mm. "Transitional" refers to when water is detected more than 30% of the time but only with a layer thickness lower than 0.1 mm. "Unstable oil wet" refers to when water is detected less than 30% of the time with layer thickness larger than 0.1 mm. "Unstable water wet" refers to when water is detected between 30% and 70% of the time with layer thickness larger than 0.1 mm. "Water wet" refers to when water is detected more than 70% of the time with layer thickness larger than 0.1 mm.

FIGS. 19A and 19B, 20A and 20B, and 21A and 21B show the measured phase wetting regimes for 1%, 5% and 10% water cut, respectively. In the case for water wet, unstable water wet and unstable oil wet regimes, the estimated time-averaged water layer thickness is also apprised in ranges to illustrate their variation with flow conditions (e.g., hollow inverted triangles indicate average water layer thicknesses between 0.1 mm and 0.5 mm).

An oil wet regime can be achieved by increasing both superficial liquid and gas velocities. Superficial liquid velocity plays a more important role since a relatively small variation of this parameter is needed to fully disperse transported water when compared to the effect of superficial gas velocity, as seen from the slope of the experimental oil wet to water wet transition indicated as dashed lines in FIGS. 19A-21B. Either unstable water wet or unstable oil wet is seen close to the phase wetting transition boundary. Intermittent formation and entrainment of water layers is expected in slug flow, as discussed above. Detected water layers are relatively thin on average (e.g., between 0.1 mm and 0.5 mm) for these flow conditions, and become thicker for lower superficial liquid and gas velocities where water drop-out is favored.

Larger superficial liquid and gas velocities are required to fully disperse the water phase when water cut increases. It is noteworthy that water wetting can be avoided at superficial liquid velocities as low as 0.5 m/s for 1% water cut, provided that superficial gas velocity is larger than 3 m/s. On the other hand, superficial liquid velocities as high as 1.5 m/s and superficial gas velocities of 2 m/s or more may be desirable to avoid water segregation at the pipe bottom for water cuts of 5% and 10%.

While the present invention has been illustrated by the description of various embodiments thereof, and while the embodiments have been described in considerable detail, it is not intended to restrict or in any way limit the scope of the appended claims to such detail. Thus, the various features discussed herein may be used alone or in any combination. Additional advantages and modifications will readily appear to those skilled in the art. The present invention in its broader aspects is therefore not limited to the specific details and illustrative examples shown and described. Accordingly, departures may be made from such details without departing from the scope of the general inventive concept.

What is claimed is:

1. A method of monitoring water wetting, the method comprising:
mounting at least one probe including at least two electrodes to a conduit having a mixture including oil and water flowing therethrough;
exciting the at least two electrodes with an AC voltage and a predetermined frequency;
measuring an impedance between the at least two electrodes; and
detecting a water layer in contact with the conduit based on the measured impedance; and
determining an oil wet to water wet transition boundary in the conduit relative to the at least two electrodes by the measured impedance,
wherein mounting the at least one probe includes flush-mounting the at least one probe to the conduit.

2. The method of claim 1 wherein the predetermined frequency is between approximately 10 kHz and approximately 1 MHz.

3. The method of claim 2, wherein the predetermined frequency is approximately 20 kHz.

4. The method of claim 1, wherein the AC voltage is between approximately 5 mV and approximately 500 mV.

5. The method of claim 4, wherein the AC voltage is approximately 10 mV rms.

6. The method of claim 1, wherein mounting the at least one probe includes mounting the at least one probe such that the at least two electrodes are concentrically mounted in the at least one probe.

7. The method of claim 1, wherein mounting the at least one probe includes mounting a plurality of probes arranged circumferentially about the conduit.

8. The method of claim 7, wherein mounting the plurality of probes includes mounting the plurality of probes such that the plurality of probes are angularly displaced from each other by approximately 45°.

9. The method of claim 1, further comprising determining a thickness of the detected water layer.

10. The method of claim 1, wherein detecting a water layer occurs within less than one second after measuring an impedance.

11. The method of claim 1, wherein mounting at least one probe includes mounting the at least one probe to a conduit having a mixture including oil, water, and gas flowing therethrough.

12. A method of detecting phase wetting in a pipe comprising measuring a frequency impedance response of a two concentric electrode probe flush mounted in the pipe, and further comprising determining an oil wet to water wet transition boundary in the pipe relative to the two concentric electrode probe by quantifying time averaged impedance values.

13. The method of claim 12, further comprising determining a thickness of a water layer.

* * * * *